(12) United States Patent
Palmowski et al.

(10) Patent No.: US 12,303,221 B2
(45) Date of Patent: *May 20, 2025

(54) SINGLE-ARM ROBOTIC DEVICE WITH COMPACT JOINT DESIGN AND RELATED SYSTEMS AND METHODS

(71) Applicant: Board of Regents of the University of Nebraska, Lincoln, NE (US)

(72) Inventors: Joseph Palmowski, Pasadena, CA (US); Shane Farritor, Lincoln, NE (US)

(73) Assignee: Board of Regents of the University of Nebraska, Lincoln, NE (US)

(*) Notice: Subject to any disclaimer, the term of this patent is extended or adjusted under 35 U.S.C. 154(b) by 0 days.

This patent is subject to a terminal disclaimer.

(21) Appl. No.: 18/607,863

(22) Filed: Mar. 18, 2024

(65) Prior Publication Data
US 2024/0252264 A1    Aug. 1, 2024

Related U.S. Application Data

(63) Continuation of application No. 17/980,665, filed on Nov. 4, 2022, now Pat. No. 11,950,867, which is a
(Continued)

(51) Int. Cl.
*B25J 9/12*    (2006.01)
*A61B 34/30*    (2016.01)
(Continued)

(52) U.S. Cl.
CPC ............... *A61B 34/30* (2016.02); *B25J 9/102* (2013.01); *B25J 9/126* (2013.01); *B25J 17/0258* (2013.01); *A61B 2034/305* (2016.02)

(58) Field of Classification Search
CPC .... A61B 23/30; A61B 2034/305; B25J 9/102; B25J 9/126; B25J 9/0021; B25J 9/06;
(Continued)

(56) References Cited

U.S. PATENT DOCUMENTS 2,858,947 A    11/1958    Chapman, Jr.
3,817,403 A    6/1974    Glachet et al.
(Continued)

FOREIGN PATENT DOCUMENTS

CA    2918531 A1    1/2015
CN    101120888 A    2/2008
(Continued)

OTHER PUBLICATIONS

Begos et al., "Laparoscopic Cholecystectomy: From Gimmick to Gold Standard," J Clin Gastroenterol, 1994; 19(4):325-330.
(Continued)

*Primary Examiner* — T. Scott Fix
(74) *Attorney, Agent, or Firm* — Fredrikson & Byron, P.A.

(57) ABSTRACT

Disclosed herein are various robotic surgical devices and systems that include first and second elongate bodies, first and second driveshafts disposed through the second elongate body, and an in-line shoulder joint with a robotic arm coupled thereto. In certain implementations, the in-line shoulder joint has a differential yoke and a dual shaft disposed within the yoke lumen.

20 Claims, 10 Drawing Sheets

Related U.S. Application Data continuation of application No. 17/236,489, filed on Apr. 21, 2021, now Pat. No. 11,504,196, which is a continuation of application No. 16/241,263, filed on Jan. 7, 2019, now Pat. No. 11,013,564.

(60) Provisional application No. 62/614,127, filed on Jan. 5, 2018.

(51) Int. Cl.
*B25J 9/10* (2006.01)
*B25J 17/02* (2006.01)

(58) Field of Classification Search
CPC ...... B25J 17/0258; B25J 17/025; B25J 17/00; B25J 17/0266; B25J 17/0283; F16C 1/02; F16C 1/04
USPC ...................................................... 74/490.03
See application file for complete search history.

(56) References Cited

U.S. PATENT DOCUMENTS

| | | |
|---|---|---|
| 3,870,264 A | 3/1975 | Robinson |
| 3,922,930 A | 12/1975 | Fletcher et al. |
| 3,971,266 A | 7/1976 | Inakura et al. |
| 3,989,952 A | 11/1976 | Hohmann |
| 4,246,661 A | 1/1981 | Pinson |
| 4,258,716 A | 3/1981 | Sutherland |
| 4,278,077 A | 7/1981 | Mizumoto |
| 4,353,677 A | 10/1982 | Susnjara et al. |
| 4,538,594 A | 9/1985 | Boebel et al. |
| 4,568,311 A | 2/1986 | Miyake |
| 4,576,545 A | 3/1986 | Maeda |
| 4,623,183 A | 11/1986 | Aomori |
| 4,636,138 A | 1/1987 | Gorman |
| 4,645,409 A | 2/1987 | Gorman |
| 4,684,313 A | 8/1987 | Minematsu et al. |
| 4,736,645 A | 4/1988 | Zimmer |
| 4,762,455 A | 8/1988 | Coughlan et al. |
| 4,771,652 A | 9/1988 | Zimmer |
| 4,852,391 A | 8/1989 | Ruch et al. |
| 4,854,808 A | 8/1989 | Bruno |
| 4,896,015 A | 1/1990 | Taboada et al. |
| 4,897,014 A | 1/1990 | Tietze |
| 4,922,755 A | 5/1990 | Oshiro et al. |
| 4,922,782 A | 5/1990 | Kawai |
| 4,984,959 A | 1/1991 | Kato |
| 4,990,050 A | 2/1991 | Tsuge et al. |
| 5,019,968 A | 5/1991 | Wang et al. |
| 5,036,724 A | 8/1991 | Rosheim |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | Mcewen et al. |
| 5,217,003 A | 6/1993 | Wilk |
| 5,263,382 A | 11/1993 | Brooks et al. |
| 5,271,384 A | 12/1993 | Mcewen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,305,653 A | 4/1994 | Ohtani et al. |
| 5,307,447 A | 4/1994 | Asano et al. |
| 5,353,807 A | 10/1994 | Demarco |
| 5,363,935 A | 11/1994 | Schempf et al. |
| 5,372,147 A | 12/1994 | Lathrop, Jr. et al. |
| 5,382,885 A | 1/1995 | Salcudean et al. |
| 5,388,528 A | 2/1995 | Pelrine et al. |
| 5,397,323 A | 3/1995 | Taylor et al. |
| 5,436,542 A | 7/1995 | Petelin et al. |
| 5,441,494 A | 8/1995 | Ortiz |
| 5,456,673 A | 10/1995 | Ziegler et al. |
| 5,458,131 A | 10/1995 | Wilk |
| 5,458,583 A | 10/1995 | Mcneely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Shinji et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,667,354 A | 9/1997 | Nakazawa |
| 5,672,168 A | 9/1997 | De La Torre et al. |
| 5,674,030 A | 10/1997 | Sigel |
| 5,728,599 A | 3/1998 | Rostoker et al. |
| 5,736,821 A | 4/1998 | Suyama |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,833,656 A | 11/1998 | Smith et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,377 A | 4/1999 | Smith et al. |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,954,692 A | 9/1999 | Smith et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,086,529 A | 7/2000 | Arndt |
| 6,102,850 A | 8/2000 | Wang et al. |
| 6,106,521 A | 8/2000 | Blewett et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |

(56) References Cited

U.S. PATENT DOCUMENTS

| | | |
|---|---|---|
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minor et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Okamoto et al. |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,450,992 B1 | 9/2002 | Cassidy |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Tierney et al. |
| 6,493,608 B1 | 12/2002 | Niemeyer |
| 6,496,099 B2 | 12/2002 | Wang et al. |
| 6,497,651 B1 | 12/2002 | Kan et al. |
| 6,508,413 B2 | 1/2003 | Bauer et al. |
| 6,512,345 B2 | 1/2003 | Borenstein et al. |
| 6,522,906 B1 | 2/2003 | Salisbury et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | Mccall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury et al. |
| 6,685,648 B2 | 2/2004 | Flaherty et al. |
| 6,685,698 B2 | 2/2004 | Morley et al. |
| 6,687,571 B1 | 2/2004 | Byrne et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wang et al. |
| 6,730,021 B2 | 5/2004 | Vassiliades et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,826,977 B2 | 12/2004 | Grover et al. |
| 6,832,988 B2 | 12/2004 | Sproul |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,793 B2 | 1/2005 | Brock et al. |
| 6,852,107 B2 | 2/2005 | Wang et al. |
| 6,853,879 B2 | 2/2005 | Sunaoshi |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,963,792 B1 | 11/2005 | Green |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 6,999,852 B2 | 2/2006 | Green |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick et al. |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |

(56) References Cited

U.S. PATENT DOCUMENTS

| | | |
|---|---|---|
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | Mcbrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,155,316 B2 | 12/2006 | Sutherland et al. |
| 7,163,525 B2 | 1/2007 | Franer |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,403,836 B2 | 7/2008 | Aoyama |
| 7,438,702 B2 | 10/2008 | Hart et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,678,043 B2 | 3/2010 | Gilad |
| 7,731,727 B2 | 6/2010 | Sauer |
| 7,734,375 B2 | 6/2010 | Buehler et al. |
| 7,762,825 B2 | 7/2010 | Burbank et al. |
| 7,772,796 B2 | 8/2010 | Farritor et al. |
| 7,785,251 B2 | 8/2010 | Wilk |
| 7,785,294 B2 | 8/2010 | Hueil et al. |
| 7,785,333 B2 | 8/2010 | Miyamoto et al. |
| 7,789,825 B2 | 9/2010 | Nobis et al. |
| 7,789,861 B2 | 9/2010 | Franer |
| 7,794,494 B2 | 9/2010 | Sahatjian et al. |
| 7,865,266 B2 | 1/2011 | Moll et al. |
| 7,960,935 B2 | 6/2011 | Farritor et al. |
| 7,979,157 B2 | 7/2011 | Anvari |
| 8,021,358 B2 | 9/2011 | Doyle et al. |
| 8,179,073 B2 | 5/2012 | Farritor et al. |
| 8,231,610 B2 | 7/2012 | Jo et al. |
| 8,343,171 B2 | 1/2013 | Farritor et al. |
| 8,353,897 B2 | 1/2013 | Doyle et al. |
| 8,377,045 B2 | 2/2013 | Schena |
| 8,430,851 B2 | 4/2013 | Mcginley et al. |
| 8,604,742 B2 | 12/2013 | Farritor et al. |
| 8,636,686 B2 | 1/2014 | Minnelli et al. |
| 8,679,096 B2 | 3/2014 | Farritor et al. |
| 8,827,337 B2 | 9/2014 | Murata et al. |
| 8,828,024 B2 | 9/2014 | Farritor et al. |
| 8,834,488 B2 | 9/2014 | Farritor et al. |
| 8,864,652 B2 | 10/2014 | Diolaiti et al. |
| 8,888,687 B2 | 11/2014 | Ostrovsky et al. |
| 8,968,332 B2 | 3/2015 | Farritor et al. |
| 8,974,440 B2 | 3/2015 | Farritor et al. |
| 8,986,196 B2 | 3/2015 | Larkin et al. |
| 9,010,214 B2 | 4/2015 | Markvicka et al. |
| 9,060,781 B2 | 6/2015 | Farritor et al. |
| 9,089,256 B2 | 7/2015 | Tognaccini et al. |
| 9,089,353 B2 | 7/2015 | Farritor et al. |
| 9,138,129 B2 | 9/2015 | Diolaiti |
| 9,198,728 B2 | 12/2015 | Wang et al. |
| 9,516,996 B2 | 12/2016 | Diolaiti et al. |
| 9,579,088 B2 | 2/2017 | Farritor et al. |
| 9,649,020 B2 | 5/2017 | Finlay |
| 9,717,563 B2 | 8/2017 | Tognaccini et al. |
| 9,743,987 B2 | 8/2017 | Farritor et al. |
| 9,757,187 B2 | 9/2017 | Farritor et al. |
| 9,770,305 B2 | 9/2017 | Farritor et al. |
| 9,789,608 B2 | 10/2017 | Itkowitz et al. |
| 9,814,640 B1 | 11/2017 | Khaligh |
| 9,816,641 B2 | 11/2017 | Bock-Aronson et al. |
| 9,849,586 B2 | 12/2017 | Rosheim |
| 9,857,786 B2 | 1/2018 | Cristiano |
| 9,888,966 B2 | 2/2018 | Farritor et al. |
| 9,956,043 B2 | 5/2018 | Farritor et al. |
| 10,008,017 B2 | 6/2018 | Itkowitz et al. |
| 10,111,711 B2 | 10/2018 | Farritor et al. |
| 10,137,575 B2 | 11/2018 | Itkowitz et al. |
| 10,159,533 B2 | 12/2018 | Moll et al. |
| 10,220,522 B2 | 3/2019 | Rockrohr |
| 10,258,425 B2 | 4/2019 | Mustufa et al. |
| 10,307,199 B2 | 6/2019 | Farritor et al. |
| 10,342,561 B2 | 7/2019 | Farritor et al. |
| 10,368,952 B2 | 8/2019 | Tognaccini et al. |
| 10,398,516 B2 | 9/2019 | Jackson et al. |
| 10,470,828 B2 | 11/2019 | Markvicka et al. |
| 10,507,066 B2 | 12/2019 | Dimaio et al. |
| 10,555,775 B2 | 2/2020 | Hoffman et al. |
| 10,582,973 B2 | 3/2020 | Wilson et al. |
| 10,695,137 B2 | 6/2020 | Farritor et al. |
| 10,729,503 B2 | 8/2020 | Cameron |
| 10,737,394 B2 | 8/2020 | Itkowitz et al. |
| 10,751,136 B2 | 8/2020 | Farritor et al. |
| 10,751,883 B2 | 8/2020 | Nahum |
| 10,806,538 B2 | 10/2020 | Farritor et al. |
| 10,966,700 B2 | 4/2021 | Farritor et al. |
| 11,032,125 B2 | 6/2021 | Farritor et al. |
| 11,298,195 B2 | 4/2022 | Ye et al. |
| 11,382,702 B2 | 7/2022 | Tognaccini et al. |
| 11,529,201 B2 | 12/2022 | Mondry et al. |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszko et al. |
| 2002/0038077 A1 | 3/2002 | De La Torre et al. |
| 2002/0065507 A1 | 5/2002 | Zadno-Azizi |
| 2002/0091374 A1 | 7/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0109780 A1 | 6/2003 | Coste-Maniere et al. |
| 2003/0114731 A1 | 6/2003 | Cadeddu et al. |
| 2003/0135203 A1 | 7/2003 | Wang et al. |
| 2003/0139742 A1 | 7/2003 | Wampler et al. |
| 2003/0144656 A1 | 7/2003 | Ocel et al. |
| 2003/0159535 A1 | 8/2003 | Grover et al. |
| 2003/0167000 A1 | 9/2003 | Mullick et al. |

(56) References Cited

U.S. PATENT DOCUMENTS

| | | |
|---|---|---|
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0225479 A1 | 12/2003 | Waled |
| 2003/0229268 A1 | 12/2003 | Uchiyama et al. |
| 2003/0229338 A1 | 12/2003 | Irion et al. |
| 2003/0230372 A1 | 12/2003 | Schmidt |
| 2004/0024311 A1 | 2/2004 | Quaid, III |
| 2004/0034282 A1 | 2/2004 | Quaid, III |
| 2004/0034283 A1 | 2/2004 | Quaid, III |
| 2004/0034302 A1 | 2/2004 | Abovitz et al. |
| 2004/0050394 A1 | 3/2004 | Jin |
| 2004/0070822 A1 | 4/2004 | Takayama et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth |
| 2004/0138525 A1 | 7/2004 | Saadat et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0070850 A1 | 3/2005 | Albrecht |
| 2005/0083460 A1 | 4/2005 | Hattori et al. |
| 2005/0095650 A1 | 5/2005 | Julius et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0177026 A1 | 8/2005 | Hoeg et al. |
| 2005/0234294 A1 | 10/2005 | Saadat et al. |
| 2005/0234435 A1 | 10/2005 | Layer |
| 2005/0272977 A1 | 12/2005 | Saadat et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0079889 A1 | 4/2006 | Scott |
| 2006/0100501 A1 | 5/2006 | Berkelman et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0189845 A1 | 8/2006 | Maahs et al. |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258938 A1 | 11/2006 | Hoffman et al. |
| 2006/0258954 A1 | 11/2006 | Timberlake et al. |
| 2006/0261770 A1 | 11/2006 | Kishi et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0088277 A1 | 4/2007 | Mcginley et al. |
| 2007/0088340 A1 | 4/2007 | Brock et al. |
| 2007/0106113 A1 | 5/2007 | Ravo |
| 2007/0106317 A1 | 5/2007 | Shelton et al. |
| 2007/0123748 A1 | 5/2007 | Meglan |
| 2007/0135803 A1 | 6/2007 | Belson |
| 2007/0142725 A1 | 6/2007 | Hardin et al. |
| 2007/0156019 A1 | 7/2007 | Larkin et al. |
| 2007/0156211 A1 | 7/2007 | Wood et al. |
| 2007/0167955 A1 | 7/2007 | Arnault De La Menardiere et al. |
| 2007/0225633 A1 | 9/2007 | Wood et al. |
| 2007/0225634 A1 | 9/2007 | Wood et al. |
| 2007/0241714 A1 | 10/2007 | Okeynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2007/0287884 A1 | 12/2007 | Schena |
| 2008/0004634 A1 | 1/2008 | Farritor et al. |
| 2008/0015565 A1 | 1/2008 | Davison |
| 2008/0015566 A1 | 1/2008 | Livneh |
| 2008/0021440 A1 | 1/2008 | Solomon |
| 2008/0033569 A1 | 2/2008 | Ferren et al. |
| 2008/0045803 A1 | 2/2008 | Williams et al. |
| 2008/0058835 A1 | 3/2008 | Farritor et al. |
| 2008/0058989 A1 | 3/2008 | Oleynikov et al. |
| 2008/0071289 A1 | 3/2008 | Cooper et al. |
| 2008/0071290 A1 | 3/2008 | Larkin et al. |
| 2008/0103440 A1 | 5/2008 | Ferren et al. |
| 2008/0109014 A1 | 5/2008 | De La Pena |
| 2008/0111513 A1 | 5/2008 | Farritor et al. |
| 2008/0119870 A1 | 5/2008 | Williams |
| 2008/0132890 A1 | 6/2008 | Woloszko et al. |
| 2008/0161804 A1 | 7/2008 | Rioux et al. |
| 2008/0164079 A1 | 7/2008 | Jacobsen |
| 2008/0168639 A1 | 7/2008 | Otake et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0002414 A1 | 1/2009 | Shibata et al. |
| 2009/0012532 A1 | 1/2009 | Blackwell et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | de la Pena |
| 2009/0163929 A1 | 6/2009 | Yeung et al. |
| 2009/0171373 A1 | 7/2009 | Farritor et al. |
| 2009/0192524 A1 | 7/2009 | Itkowitz et al. |
| 2009/0234369 A1 | 9/2009 | Bax et al. |
| 2009/0236400 A1 | 9/2009 | Cole et al. |
| 2009/0240246 A1 | 9/2009 | Deville et al. |
| 2009/0247821 A1 | 10/2009 | Rogers |
| 2009/0248038 A1 | 10/2009 | Blumenkranz et al. |
| 2009/0281377 A1 | 11/2009 | Acosta et al. |
| 2009/0299143 A1 | 12/2009 | Conlon et al. |
| 2009/0305210 A1 | 12/2009 | Guru et al. |
| 2009/0326322 A1 | 12/2009 | Diolaiti |
| 2010/0010294 A1 | 1/2010 | Conlon et al. |
| 2010/0016659 A1 | 1/2010 | Weitzner |
| 2010/0016853 A1 | 1/2010 | Burbank |
| 2010/0026347 A1 | 2/2010 | Iizuka |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0101346 A1 | 4/2010 | Johnson et al. |
| 2010/0130986 A1 | 5/2010 | Mailloux et al. |
| 2010/0139436 A1 | 6/2010 | Kawashima et al. |
| 2010/0185212 A1 | 7/2010 | Sholev |
| 2010/0198231 A1 | 8/2010 | Scott |
| 2010/0204713 A1 | 8/2010 | Ruiz Morales |
| 2010/0245549 A1 | 9/2010 | Allen et al. |
| 2010/0250000 A1 | 9/2010 | Blumenkranz et al. |
| 2010/0262162 A1 | 10/2010 | Omori |
| 2010/0263470 A1 | 10/2010 | Bannasch et al. |
| 2010/0274079 A1 | 10/2010 | Kim et al. |

(56) References Cited

U.S. PATENT DOCUMENTS

| | | | |
|---|---|---|---|
| 2010/0292691 A1 | 11/2010 | Brogna | |
| 2010/0301095 A1 | 12/2010 | Shelton, IV et al. | |
| 2010/0318059 A1 | 12/2010 | Farritor et al. | |
| 2010/0331856 A1 | 12/2010 | Carlson et al. | |
| 2011/0015569 A1 | 1/2011 | Kirschenman et al. | |
| 2011/0020779 A1 | 1/2011 | Hannaford et al. | |
| 2011/0071347 A1 | 3/2011 | Rogers et al. | |
| 2011/0071544 A1 | 3/2011 | Steger et al. | |
| 2011/0075693 A1 | 3/2011 | Kuramochi et al. | |
| 2011/0077478 A1 | 3/2011 | Freeman et al. | |
| 2011/0082365 A1 | 4/2011 | Mcgrogan et al. | |
| 2011/0098529 A1 | 4/2011 | Ostrovsky et al. | |
| 2011/0107866 A1 | 5/2011 | Oka et al. | |
| 2011/0152615 A1 | 6/2011 | Schostek et al. | |
| 2011/0224605 A1 | 9/2011 | Farritor et al. | |
| 2011/0230894 A1 | 9/2011 | Simaan et al. | |
| 2011/0237890 A1 | 9/2011 | Farritor et al. | |
| 2011/0238079 A1 | 9/2011 | Hannaford et al. | |
| 2011/0238080 A1 | 9/2011 | Ranjit et al. | |
| 2011/0264078 A1 | 10/2011 | Lipow et al. | |
| 2011/0270443 A1 | 11/2011 | Kamiya et al. | |
| 2011/0276046 A1 | 11/2011 | Heimbecher et al. | |
| 2012/0016175 A1 | 1/2012 | Roberts et al. | |
| 2012/0029727 A1 | 2/2012 | Malik | |
| 2012/0035582 A1 | 2/2012 | Nelson et al. | |
| 2012/0059392 A1 | 3/2012 | Diolaiti | |
| 2012/0078053 A1 | 3/2012 | Phee et al. | |
| 2012/0109150 A1 | 5/2012 | Blackwell et al. | |
| 2012/0116362 A1 | 5/2012 | Kieturakis | |
| 2012/0179168 A1 | 7/2012 | Farritor et al. | |
| 2012/0221147 A1 | 8/2012 | Goldberg et al. | |
| 2012/0253515 A1 | 10/2012 | Coste-Maniere et al. | |
| 2013/0001970 A1 | 1/2013 | Suyama et al. | |
| 2013/0041360 A1 | 2/2013 | Farritor et al. | |
| 2013/0055560 A1 | 3/2013 | Nakasugi et al. | |
| 2013/0125696 A1 | 5/2013 | Long | |
| 2013/0131695 A1 | 5/2013 | Scarfogliero et al. | |
| 2013/0178867 A1 | 7/2013 | Farritor et al. | |
| 2013/0282023 A1 | 10/2013 | Burbank et al. | |
| 2013/0304084 A1 | 11/2013 | Beira et al. | |
| 2013/0325030 A1 | 12/2013 | Hourtash et al. | |
| 2013/0325181 A1 | 12/2013 | Moore | |
| 2013/0345717 A1 | 12/2013 | Markvicka et al. | |
| 2013/0345718 A1 | 12/2013 | Crawford et al. | |
| 2014/0039515 A1 | 2/2014 | Mondry et al. | |
| 2014/0046340 A1 | 2/2014 | Wilson et al. | |
| 2014/0055489 A1 | 2/2014 | Itkowitz et al. | |
| 2014/0058205 A1 | 2/2014 | Frederick et al. | |
| 2014/0100587 A1 | 4/2014 | Farritor et al. | |
| 2014/0137687 A1 | 5/2014 | Nogami et al. | |
| 2014/0195052 A1 | 7/2014 | Tsusaka et al. | |
| 2014/0221749 A1 | 8/2014 | Grant et al. | |
| 2014/0232824 A1 | 8/2014 | Dimaio et al. | |
| 2014/0276944 A1 | 9/2014 | Farritor et al. | |
| 2014/0303434 A1* | 10/2014 | Farritor | A61B 1/3132 600/102 |
| 2014/0371762 A1 | 12/2014 | Farritor et al. | |
| 2015/0051446 A1 | 2/2015 | Farritor et al. | |
| 2015/0157191 A1 | 6/2015 | Phee et al. | |
| 2015/0223896 A1 | 8/2015 | Farritor et al. | |
| 2015/0297299 A1 | 10/2015 | Yeung et al. | |
| 2016/0066999 A1 | 3/2016 | Forgione et al. | |
| 2016/0135898 A1 | 5/2016 | Frederick et al. | |
| 2016/0291571 A1 | 10/2016 | Cristiano | |
| 2016/0303745 A1* | 10/2016 | Rockrohr | B25J 17/0258 |
| 2017/0014197 A1 | 1/2017 | Mccrea et al. | |
| 2017/0035526 A1 | 2/2017 | Farritor et al. | |
| 2017/0078583 A1 | 3/2017 | Haggerty et al. | |
| 2017/0252096 A1 | 9/2017 | Felder et al. | |
| 2017/0354470 A1 | 12/2017 | Farritor et al. | |
| 2018/0132956 A1 | 5/2018 | Cameron | |
| 2018/0153578 A1 | 6/2018 | Cooper et al. | |
| 2018/0153634 A1 | 6/2018 | Zemlok et al. | |
| 2018/0338777 A1 | 11/2018 | Bonadio et al. | |
| 2019/0059983 A1 | 2/2019 | Germain et al. | |
| 2019/0090965 A1 | 3/2019 | Farritor et al. | |
| 2019/0209262 A1 | 7/2019 | Mustufa et al. | |
| 2019/0327394 A1 | 10/2019 | Ramirez Luna et al. | |
| 2020/0138534 A1 | 5/2020 | Garcia Kilroy et al. | |
| 2020/0214775 A1 | 7/2020 | Farritor et al. | |
| 2020/0330175 A1 | 10/2020 | Cameron | |
| 2020/0368915 A1 | 11/2020 | Itkowitz et al. | |

FOREIGN PATENT DOCUMENTS

| | | |
|---|---|---|
| CN | 102499759 A | 6/2012 |
| CN | 102821918 A | 12/2012 |
| CN | 104523309 A | 4/2015 |
| CN | 104582600 A | 4/2015 |
| CN | 104622528 A | 5/2015 |
| CN | 204337044 U | 5/2015 |
| CN | 104786233 A | 7/2015 |
| CN | 105025826 A | 11/2015 |
| DE | 102010040405 A1 | 3/2012 |
| EP | 105656 A2 | 4/1984 |
| EP | 279591 A1 | 8/1988 |
| EP | 1354670 A1 | 10/2003 |
| EP | 2286756 A1 | 2/2011 |
| EP | 2329787 A2 | 6/2011 |
| EP | 2563261 A1 | 3/2013 |
| EP | 2684528 A1 | 1/2014 |
| EP | 2123225 B1 | 12/2014 |
| EP | 2815705 A1 | 12/2014 |
| EP | 2881046 A2 | 6/2015 |
| EP | 2937047 A1 | 10/2015 |
| JP | 59059371 A | 4/1984 |
| JP | 60001456 A | 1/1985 |
| JP | 61165061 A | 7/1986 |
| JP | 62068293 A | 3/1987 |
| JP | 01109094 A | 4/1989 |
| JP | H04144533 A | 5/1992 |
| JP | H05115425 A | 5/1993 |
| JP | H06507809 A | 9/1994 |
| JP | H06508049 A | 9/1994 |
| JP | H07016235 A | 1/1995 |
| JP | H07136173 A | 5/1995 |
| JP | H07306155 A | 11/1995 |
| JP | H08224248 A | 9/1996 |
| JP | 2001505810 A | 5/2001 |
| JP | 2002000524 A | 1/2002 |
| JP | 2003220065 A | 8/2003 |
| JP | 2004180781 A | 7/2004 |
| JP | 2004283940 A | 10/2004 |
| JP | 2004322310 A | 11/2004 |
| JP | 2004329292 A | 11/2004 |
| JP | 2009106606 A | 5/2009 |
| JP | 2009297809 A | 12/2009 |
| JP | 2010533045 A | 10/2010 |
| JP | 2010536436 A | 12/2010 |
| JP | 2011504794 A | 2/2011 |
| JP | 2011045500 A | 3/2011 |
| JP | 2011115591 A | 6/2011 |
| JP | 2012504017 A | 2/2012 |
| JP | 2012176489 A | 9/2012 |
| JP | 5418704 B1 | 2/2014 |
| JP | 2015526171 A | 9/2015 |
| JP | 2016213937 A | 12/2016 |
| JP | 2017113837 A | 6/2017 |
| WO | 9221291 A2 | 12/1992 |
| WO | 0189405 A1 | 11/2001 |
| WO | 02082979 A2 | 10/2002 |
| WO | 02100256 A2 | 12/2002 |
| WO | 2005009211 A2 | 2/2005 |
| WO | 2005044095 A1 | 5/2005 |
| WO | 2006005075 A2 | 1/2006 |
| WO | 2006052927 A2 | 5/2006 |
| WO | 2006079108 A1 | 7/2006 |
| WO | 2007011654 A1 | 1/2007 |
| WO | 2007111571 A1 | 10/2007 |
| WO | 2007149559 A2 | 12/2007 |
| WO | 2009014917 A2 | 1/2009 |
| WO | 2009023851 A1 | 2/2009 |
| WO | 2009144729 A1 | 12/2009 |
| WO | 2009158164 A1 | 12/2009 |

(56) References Cited

FOREIGN PATENT DOCUMENTS

| | | |
|---|---|---|
| WO | 2010039394 A1 | 4/2010 |
| WO | 2010042611 A1 | 4/2010 |
| WO | 2010046823 A1 | 4/2010 |
| WO | 2010050771 A2 | 5/2010 |
| WO | 2010083480 A2 | 7/2010 |
| WO | 2011075693 A1 | 6/2011 |
| WO | 2011118646 A1 | 9/2011 |
| WO | 2011135503 A1 | 11/2011 |
| WO | 2011163520 A2 | 12/2011 |
| WO | 2013009887 A1 | 1/2013 |
| WO | 2013052137 A2 | 4/2013 |
| WO | 2013106569 A2 | 7/2013 |
| WO | 2014011238 A2 | 1/2014 |
| WO | 2014025399 A1 | 2/2014 |
| WO | 2014144220 A1 | 9/2014 |
| WO | 2014146090 A1 | 9/2014 |
| WO | 2014152418 A1 | 9/2014 |
| WO | 2015009949 A2 | 1/2015 |
| WO | 2015031777 A1 | 3/2015 |
| WO | 2015088655 A1 | 6/2015 |
| WO | 2016077478 A1 | 5/2016 |
| WO | 2017024081 A1 | 2/2017 |
| WO | 2017064303 A1 | 4/2017 |
| WO | 2017201310 A1 | 11/2017 |
| WO | 2018045036 A1 | 3/2018 |

OTHER PUBLICATIONS

Fukuda et al., "Mechanism and Swimming Experiment of Micro Mobile Robot in Water," Proceedings of the 1994 IEEE International Conference on Robotics and Automation, 1994; 814-819.

Fukuda et al., "Micro Active Catheter System with Multi Degrees of Freedom," Proceedings of the IEEE International Conference on Robotics and Automation, May 1994: 2290-2295.

Bailey et al., "Complications of Laparoscopic Surgery," Quality Medical Publishers, Inc., 1995; 25 pp.

Green, "Telepresence Surgery", Jan. 1, 1995, Publisher: IEEE Engineering in Medicine and Biology.

Franklin et al., "Prospective Comparison of Open vs. Laparoscopic Colon Surgery for Carcinoma: Five-Year Results," Dis Colon Rectum, 1996; 39: S35-S46.

Guo et al., "Micro Active Guide Wire Catheter System-Characteristic Evaluation, Electrical Model* and Operability Evaluation of Micro Active Catheter," Proceedings of the 1996 IEEE International Conference on Robotics and Automation, Apr. 1996; 2226-2231.

Allendorf et al., "Postoperative Immune Function Varies Inversely with the Degree of Surgical Trauma in a Murine Model," Surgical Endoscopy, 1997; 11: 427-430.

Flynn et al., "Tomorrow's Surgery; Micro-motors and Microrobots for Minimally Invasive Procedures," Minimally Invasive Surgery & Allied Technologies, 1998, 7(4): pp. 343-352.

Calafiore et al., "Multiple Arterial Conduits Without Cardiopulmonary Bypass: Early Angiographic Results," Ann Thorac Surg, 1999; 67: 450-456.

Cuschieri, "Technology for Minimal Access Surgery," BMJ, 1999; 319: 1-6.

Faraz et al., "Engineering Approaches to Mechanical and Robotic Design for Minimally Invasive Surgery (MIS)," Kluwer Academic Publishers (Boston), 2000, 13 pp.

Fearing et al., "Wing Transmission for a Micromechanical Flying Insect," Proceedings of the 2000 IEEE International Conference on Robotics & Automation, Apr. 2000: 1509-1516.

Gong et al., "Wireless endoscopy," Gastrointestinal Endoscopy 2000; 51 (6): 725-729.

Heikkinen et al., "Comparison of laparoscopic and open Nissen fundoplication two years after operation: A prospective randomized trial," Surgical Endoscopy, 2000; 14:1019-1023.

Abbou et al., "Laparoscopic Radical Prostatectomy with a Remote Controlled Robot," The Journal of Urology, Jun. 2001; 165: 1964-1966.

Bauer et al., "Case Report: Remote Percutaneous Renal Access Using a New Automated Telesurgical Robotic System," Telemedicine Journal and e-Health 2001; (4): 341-347.

Breda et al., "Future developments and perspectives in laparoscopy," Eur. Urology 2001: 40(1): 84-91.

Cavusoglu et al., "Telesurgery and Surgical Simulation: Haptic Interfaces to Real and Virtual Surgical Environments," In Mclaughlin, M. L., Hespanha, J. P., and Sukhatme, G., editors. Touch in virtual environments, IMSC Series in Multimedia 2001; 28 pp.

Ballantyne, "Robotic Surgery, Telerobotic Surgery, Telepresence, and Telementoring," Surgical Endoscopy, 2002; 16: 1389-1402.

Cleary et al., "State of the Art in Surgical Robotics: Clinical Applications and Technology Challenges", "Computer Aided Surgery", Jan. 1, 2002, pp. 312-328, vol. 6.

Fraulob et al., "Miniature assistance module for robot-assisted heart surgery," Biomed. Tech. 2002; 47 Suppl. 1, Pt. 1: 12-5.

Guber et al., "Miniaturized Instrument Systems for Minimally Invasive Diagnosis and Therapy," Biomedizinische Technic, 2002; Band 47, Erganmngsband 1: 198-201.

Guo et al., "Fish-like Underwater Microrobot with 3 DOF," Proceedings of the 2002 IEEE International Conference on Robotics & Automation, May 2002; 738-743.

Cavusoglu et al., "Robotics for Telesurgery: Second Generation BerkeleyIUCSF Laparoscopic Telesurgical Workstation and Looking Towards the Future Applications," Industrial Robot: An International Journal, 2003; 30(1): 22-29.

Chanthasopeephan et al. (2003), "Measuring Forces in Liver Cutting: New Equipment and Experimental Results," Annals of Biomedical Engineering 31: 1372-1382.

Dakin et al., "Comparison of laparoscopic skills performance between standard instruments and two surgical robotic systems," Surg Endosc., 2003; 17: 574-579.

Falcone et al., "Robotic Surgery," Clin. Obstet. Gynecol. 2003; 46(1): 37-43.

Fireman et al., "Diagnosing small bowel Crohn's disease with wireless capsule endoscopy," Gut 2003; 52:390-392.

Franzino, "The Laprotek Surgical System and the Next Generation of Robotics," Surg. Clin. North Am, 2003; 83(6): 1317-1320.

Ang, "Active Tremor Compensation in Handheld Instrument for Microsurgery," Doctoral dissertation, tech report CMU-RI-TR-04-28, Robotics Institute, Carnegie Mellon University, May 2004, 150 pp.

Albers et al., Design and development process of a humanoid robot upper body through experimentation, 2004, IEEE, p. 77-92 (Year: 2004).

Breedveld et al., "Design of Steerable Endoscopes to Improve the Visual Perception of Depth During Laparoscopic Surgery," ASME, Jan. 2004; 126: 1-5.

Breedveld et al., "Locomotion through the Intestine by means of Rolling Stents," Proceedings of the ASME Design Engineering Technical Conferences, 2004.

Camarillo et al., "Robotic Technology in Surgery: Past, Present, and Future," The American Journal of Surgery, 2004; 188: 2S-15.

Glukhovsky et al., "The development and application of wireless capsule endoscopy," Int. J. Med. Robot. Comput. Assist. Surgery, 2004; 1(1): 114-123.

Hanly et al., "Robotic Abdominal Surgery," The American Journal of Surgery, 2004; 188 (Suppl. to Oct. 1994); 19S-26S.

Hanly et al., "Value of the SAGES Learning Center in introducing new technology," Surgical Endoscopy, 2004; 19 (4): 477-483.

Choi et al., "Flexure-based Manipulator for Active Handheld Microsurgical Instrument," Proceedings of the 27th Annual International Conference of the IEEE Engineering in Medicine and Biology Society (EMBS), Sep. 2005.

Dumpert et al., "Improving In Vivo Robot Vision Quality," in the Proceedings of Medicine Meets Virtual Reality, Long Beach, CA, Jan. 26-29, 2005.

Atmel 80C5X2 Core, http://www.atmel.com, 2006, 186 pp.

Abbott et al., "Design of an Endoluminal NOTES Robotic System," Proceedings of the 2007 IEEE/RSJ Int'l Conf. on Intelligent Robot Systems, San Diego, CA, Oct. 29-Nov. 2, 2007: 410-416.

Berg et al., "Surgery with Cooperative Robots," Medicine Meets Virtual Reality, Feb. 2007; 1 pg.

(56) References Cited

OTHER PUBLICATIONS

Crystal Eyes, http://www.reald.com, 2007 (Stereo 3D visualization for CAVEs, theaters and immersive environments), 1 pg.
Dumpert et al., "Stereoscopic In Vivo Surgical Robots," IEEE Sensors Special Issue on In Vivo Sensors for Medicine, Jan. 2007, 10 pp.
Grady, "Doctors Try New Surgery for Gallbladder Removal," The New York Times, Apr. 20, 2007; 3pp.
Gopura et al., Mechanical designs of active upper-limb exoskeleton robots: State-of-the-art and design difficulties, 2009, IEEE, p. 178-187 (Year: 2009).
Gopura et al., A brief review on upper extremity robotic exoskeleton systems, 2011, IEEE, p. 346-351 (Year: 2011).
Definition of Individually. Dictionary.com, retrieved on Aug. 9, 2016; Retrieved from the Internet: <http://www.dictionary.com/browse/individually>, 1 page.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committee," U.S. Food and Drug Administration, available at http://www.fda.gov, Finalized: Nov. 7, 2003; Updated: Jun. 24, 2005, 11 pp.
Southern Surgeons Club (1991), "A prospective analysis of 1518 laparoscopic cholecystectomies," N. Eng. 1 Med. 324 (16): 1073-1078.
Suzumori et al., "Development of Flexible Microactuator and its Applications to Robotics Mechanisms," Proceedings of the IEEE International Conference on Robotics and Automation, 1991: 1622-1627.
Tendick et al. (1993), "Sensing and Manipulation Problems in Endoscopic Surgery: Experiment, Analysis, and Observation," Presence 2(1): 66-81.
Sackier et al., "Robotically assisted laparoscopic surgery," Surgical Endoscopy, 1994; 8:63-6.
Stiff et al., "Long-term Pain: Less Common After Laparoscopic than Open Cholecystectomy," British Journal of Surgery, 1994; 81: 1368-1370.
Slatkin et al., "The Development of a Robotic Endoscope," Proceedings of the 1995 IEEE International Conference on Robotics and Automation, pp. 162-171, 1995.
Taylor et al., "A Telerobotic Assistant for Laparoscopic Surgery," IEEE Eng Med Biol, 1995; 279-87.
Schippers et al. (1996), "Requirements and Possibilities of Computer-Assisted Endoscopic Surgery," In: Computer Integrated Surgery: Technology and Clinical Applications, pp. 561-565.
Tendick et al., "Applications of Micromechatronics in Minimally Invasive Surgery," IEEE/ASME Transactions on Mechatronics, 1998; 3(1): 34-42.
Rosen et al., "Force Controlled and Teleoperated Endoscopic, Grasper for Minimally Invasive Surgery-Experimental Performance Evaluation," IEEE Transactions of Biomedical Engineering, Oct. 1999; 46(10): 1212-1221.
Salky, "What is the Penetration of Endoscopic Techniques into Surgical Practice?" Digestive Surgery 2000; 17:422-426.
Schurr et al., "Robotics and Telemanipulation Technologies for Endoscopic Surgery," Surgical Endoscopy, 2000; 14:375-381.
Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.
Rosen et al., "The Blue DRAGON—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.
Ruurda et al., "Robot-Assisted surgical systems: a new era in laparoscopic surgery," Ann R. Coll Surg Engl. 2002; 84: 223-226.
Ruurda et al., "Feasibility of Robot-Assisted Laparoscopic Surgery," Surgical Laparoscopy, Endoscopy & Percutaneous Techniques, 2002; 12(1):41-45.
Rosen et al., Objective Evaluation of Laparoscopic Skills Based on Haptic Information and Tool/Tissue Interactions, Computer Aided Surgery, vol. 7, Issue 1, pp. 49-61, Jul. 2002.
Satava, "Surgical Robotics: The Early Chronicles," Surgical Laparoscopy, Endoscopy & Percutaneous Techniques, 2002; 12(1):6-16.
Stoianovici et al., "Robotic Tools for Minimally Invasive Urologic Surgery", Jan. 1, 2002, pp. 1-17.
Thomann et al., "The Design of a new type of Micro Robot for the Intestinal Inspection," Proceedings of the 2002 IEEE Intl. Conference on Intelligent Robots and Systems, Oct. 2002: 1385-1390.
Riviere et al., "Toward Active Tremor Canceling in Handheld Microsurgical Instruments," IEEE Transactions on Robotics and Automation, Oct. 2003, 19(5): 793-800.
Rentschler et al., "In Vivo Robots for Laparoscopic Surgery," Studies in Health Technology and Infonnatics—Medicine Meets Virtual Reality, ISO Press, Newport Beach, CA, 2004a, 98: 316-322.
Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.
Rentschler et al., "Modeling, Analysis, and Experimental Study of In Vivo Wheeled Robotic Mobility," IEEE Transactions on Robotics, 22 (2): 308-321, 2005c.
Rentschler et al., "Toward In Vivo Mobility," Studies in Health Technology and Infonnatics—Medicine Meets Virtual Reality, ISO Press, Long Beach, CA, 2005a, III: 397-403.
Rosen et al., "Spherical Mechanism Analysis of a Surgical Robot for Minimally Invasive Surgery—Analytical and Experimental Approaches," Studies in Health Technology and Infonnatics-Medicine Meets Virtual Reality, pp. 442-448, Jan. 2005.
Smart Pill "Fastastic Voyage: Smart Pill to Expand Testing," http://www.smartpilldiagnostics.com, Apr. 13, 2005, 1 pg.
Strong et al., "Efficacy of Novel Robotic Camera vs. a Standard Laproscopic Camera," Surgical Innovation vol. 12, No. 4, Dec. 2005, Westminster Publications, Inc., pp. 315-318.
Sodeyama et al., A shoulder structure of muscle-driven humanoid with shoulder blades, 2005, IEEE, p. 1-6 (Year: 2005).
Rentschler et al., "Mechanical Design of Robotic In Vivo Wheeled Mobility," ASME Journal of Mechanical Design, 2006a; pp. 1-11, Accepted.
Rentschler et al., "Miniature in vivo robots for remote and harsh environments," IEEE Transaction on Information Technology in Biomedicine, Jan. 2006; 12(1): pp. 66-75.
Rentschler et al., "Mobile In Vivo Biopsy Robot," IEEE International Conference on Robotics and Automation, Orlando, Florida, May 2006; 4155-4160.
Rentschler et al., "Mobile In Vivo Biopsy and Camera Robot," Studies in Health and Infonnatics Medicine Meets Virtual Reality, vol. 119: 449-454, IOS Press, Long Beach, CA, 2006e.
Rentschler et al., "Mobile In Vivo Camera Robots Provide Sole Visual Feedback for Abdominal Exploration and Cholecystectomy," Journal of Surgical Endoscopy, 20-1: 135-138, 2006b.
Rentschler et al., "Natural Orifice Surgery with an Endoluminal Mobile Robot," The Society of American Gastrointestinal Endoscopic Surgeons, Dallas, TX, April 2006d.
Stefanini et al., "Modeling and Experiments on a Legged Microrobot Locomoting in a Tubular Compliant and Slippery Environment," Int. Journal of Robotics Research, vol. 25, No. 5-6, pp. 551-560, Mav-Jun. 2006.
Sharp LL-151-3D, http://www.sharp3d.com, 2006, 2 pp.
Rentschler et al., "An In Vivo Mobile Robot for Surgical Vision and Task Assistance," Journal of Medical Devices, Mar. 2007; vol. 1: 23-29.
Rentschler et al., "In vivo Robotics during the NEEMO 9 Mission," Medicine Meets Virtual Reality, Feb. 2007; 1 pg.
Schwartz, "In the Lab: Robots that Slink and Squirm," The New York Times, Mar. 27, 2007, 4 pp.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.

(56) References Cited

OTHER PUBLICATIONS

U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
Mack et al., "Present Role of Thoracoscopy in the Diagnosis and Treatment of Diseases of the Chest," Ann Thorac Surgery, 1992; 54: 403-409.
Peters, "Minimally Invasive Colectomy: Are the Potential Benefits Realized?" Dis Colon Rectum 1993; 36: 751-756.
Liem et al., "Comparison of Conventional Anterior Surgery and Laparoscopic Surgery for Inguinal-hernia Repair," New England Journal of Medicine, 1997; 336 (22): 1541-1547.
Kazemier et al. (1998), "Vascular Injuries During Laparoscopy," J. Am. Coli. Surg. 186(5): 604-5.
Palm. William. "Rapid Prototyping Primer" May 1998 (revised Jul. 30, 2002) (http://www.me.psu.edu/lamancusa/rapidpro/primer/chapter2.htm), 12 pages.
Macfarlane et al., "Force-Feedback Grasper Helps Restore the Sense of Touch in Minimally Invasive Surgery," Journal of Gastrointestinal Surgery, 1999; 3: 278-285.
Li et al. (2000), "Microvascular Anastomoses Performed in Rats Using a Microsurgical Telemanipulator," Comp. Aid. Surg., 5: 326-332.
Lshiyama et al., "Spiral-type Micro-machine for Medical Applications," 2000 International Symposium on Micromechatronics and Human Science, 2000; 65-69.
Meron, "The development of the swallowable video capsule (M2A)," Gastrointestinal Endoscopy 2000; 52 6: 817-819.
Horgan et al., "Technical Report: Robots in Laparoscopic Surgery," Journal of Laparoendoscopic & Advanced Surgical Techniques, 2001; 11(6): 415-419.
Kang et al., "Robotic Assistants Aid Surgeons During Minimally Invasive Procedures," IEEE Engineering in Medicine and Biology, Jan.-Feb. 2001: 94-104.
Lafullarde et al., "Laparoscopic Nissen Fundoplication: Five-year Results and Beyond," Arch/Surg, Feb. 2001; 136: 180-184.
Mack, "Minimally Invasive and Robotic Surgery," JAMA, Feb. 2001; 285(5): 568-572.
Peirs et al., "A miniature manipulator for integration in a self-propelling endoscope," Sensors and Actuators A, 2001, 92: 343-349.
Phee et al., "Development of Microrobotic Devices for Locomotion in the Human Gastrointestinal Tract," International Conference on Computational Intelligence, Robotics and Autonomous Systems (CI RAS 2001), Nov. 28-30, 2001, Singapore, 6 pages.
Kim, "Early Experience with Telemanipulative Robot-Assisted Laparoscopic Cholecystectomy Using da Vinci," Surgical Laparoscopy, Endoscopy & Percutaneous Techniques, 2002; 12(1): 33-40.
Leggett et al. (2002), "Aortic injury during laparoscopic Fundoplication," Surg. Endoscopy 16(2): 362.
Mei et al., "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.
Munro (2002), "Laparoscopic access: complications, technologies, and techniques," Curro Opin. Obstet. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Phee et al., "Analysis and Development of Locomotion Devices for the Gastrointestinal Tract," IEEE Transactions on Biomedical Engineering, vol. 49, No. 6, Jun. 2002: 613-616.
Orlando et al. (2003), "Needle and Trocar Injuries in Diagnostic Laparoscopy under Local Anesthesia: What Is the True Incidence of These Complications?" Journal of Laparoendoscopic & Advanced Surgical Techniques, 13(3): 181-184.
Hissink, "Olympus Medical develops capsule camera technology," Dec. 2004, accessed Aug. 29, 2007, http://www.letsgodigital.org, 3 pp.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp., 2004.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Patronik et al., "Crawling on the Heart: A Mobile Robotic Device for Minimally Invasive Cardiac Interventions," MICCAI, 2004, pp. 9-16.
Patronik et al., "Development of a Tethered Epicardial Crawler for Minimally Invasive Cardiac Therapies," IEEE, pp. 239-240, 2004.
Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004; pp. 1-9.
Jagannath et al., "Peroral transgastric endoscopic ligation of fallopian tubes with long-term survival in a porcine model," Gastrointestinal Endoscopy, 2005; 61 (3): 449-453.
Kantsevoy et al., "Endoscopic gastrojejunostomy with survival in a porcine model," Gastrointestinal Endoscopy, 2005; 62(2): 287-292.
Menciassi et al., "Shape memory alloy clamping devices of a capsule for monitoring tasks in the gastrointestinal tract," J. Micromech. Microeng, 2005; 15: 2045-2055.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
Park et al., "Experimental studies of transgastric gallbladder surgery: cholecystectomy and cholecystogastric anastomosis (videos)," Gastrointestinal Endoscopy, 2005; 61 (4): 601-606.
Patronik et al., "Preliminary evaluation of a mobile robotic device for navigation and intervention on the beating heart," Computer Aided Surgery, 10(4): 225-232, Jul. 2005.
Platt et al., "In Vivo Robotic Cameras can Enhance Imaging Capability During Laparoscopic Surgery," from the Proceedings of the Society of American Gastrointestinal Endoscopic Surgeons (SAGES) Scientific Conference, Ft. Lauderdale, FL, Apr. 13-16, 2005; 1 pg.
Kantsevoy et al., "Transgastric endoscopic splenectomy," Surgical Endoscopy, 2006; 20: 522-525.
Ko et al., "Per-Oral transgastric abdominal surgery," Chinese Journal of Digestive Diseases, 2006; 7: 67-70.
Micron, http://www.micron.com, 2006, 1/4-inch VGA NTSC/PAL CMOS Digital Image Sensor, 98 pp.
O'Neill, "Surgeon takes new route to gallbladder," The Oregonian, Jun. 2007; 2 pp.
Park et al., "Trocar-less Instrumentation for Laparoscopy: Magnetic Positioning of Intra-abdominal Camera and Retractor," Ann Surg, Mar. 2007; 245(3): 379-384.
Midday Jeff et al., "Material Handling System for Robotic natural Orifice Surgery,", Proceedings of the 2011 Design of medical Devices Conference, Apr. 12-14, 2011, Minneapolis, MN 4 pages.
Keller et al., Design of the pediatric arm rehabilitation robot ChARMin, 2014, IEEE, p. 530-535 (Year: 2014).
Qian Huan et al., "Multi-joint Single-wound Minimally Invasive Abdominal Surgery Robot Design," Mechanical Design and Manufacturing, May 8, 2014, pp. 134-137.

(56) References Cited

OTHER PUBLICATIONS

Lou Cubrich, "A Four-DOF Laparo-Endoscopic Single Site Platform for Rapidly-Developing Next Generation Surgical Robotics", Journal of Medical Robotics Research, vol. 1, No. 4, 2016, 165006-1-165006-15.
In vivo Mobile Surgical Robotic Task Assistance, "1 pg.".
Wolfe et al. (1991), Endoscopic Cholecystectomy: An analysis of Complications, Arch. Surg. 1991; 126: 1192-1196.
Way et al., Editors, "Fundamentals of Laparoscopic Surgery," Churchill Livingstone Inc., 1995; 14 pp.
Worn et al., "Espirit Project No. 33915: Miniaturised Robot for Micro Manipulation (MINIMAN)," Nov. 1998, http://www.ipr.ira.ujka.de/-microbot/miniman.
Yu et al., "Microrobotic Cell Injection," Proceedings of the 2001 IEEE International Conference on Robotics and Automation, May 2001: 620-625.
Yu, BSN, RN, "M2ATM Capsule Endoscopy A Breakthrough Diagnostic Tool for Small Intestine Imagining," vol. 25, No. 1, 2001, Gastroenterology Nursing, pp. 24-27.
Xu et al., "System Design of an Insertable Robotic Effector Platform for Single Access (SPA) Surgery", The 2009 IEEE/RSJ International Conference on Intelligent Robots and Systems, Oct. 11-15, 2009, St. Louis MO USA pp. 5546-5552.
U.S. Appl. No. 61/030,588, filed Feb. 22, 2008.
U.S. Appl. No. 61/030,617, filed Feb. 22, 2008.
Asada et al. "Introduction" Direct-Drive Robots: Theory and Practice, MIT Press, 1987, pp. 1-17.

* cited by examiner

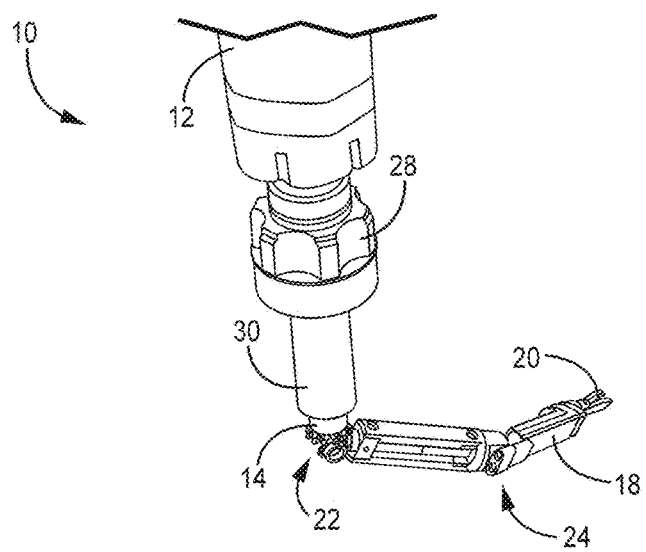
FIG. 1A
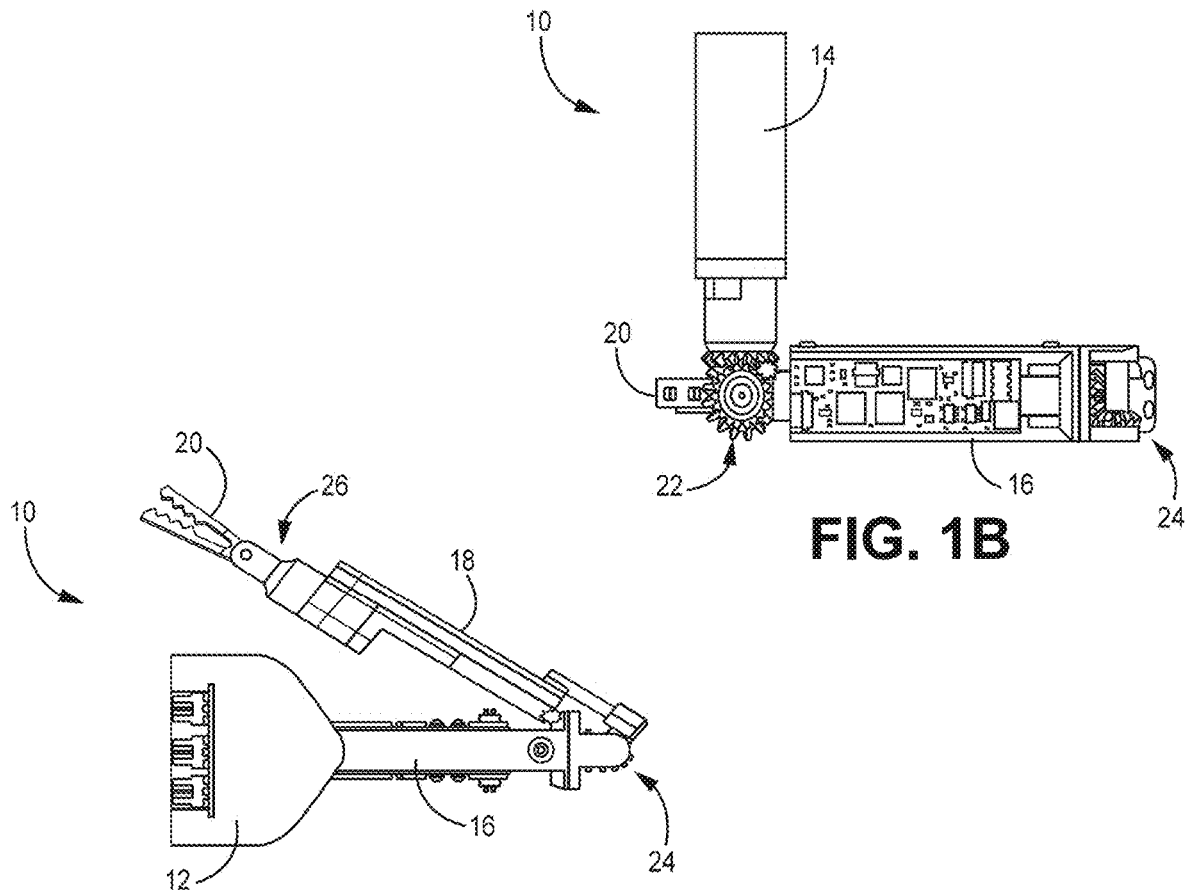
FIG. 1B
FIG. 1C

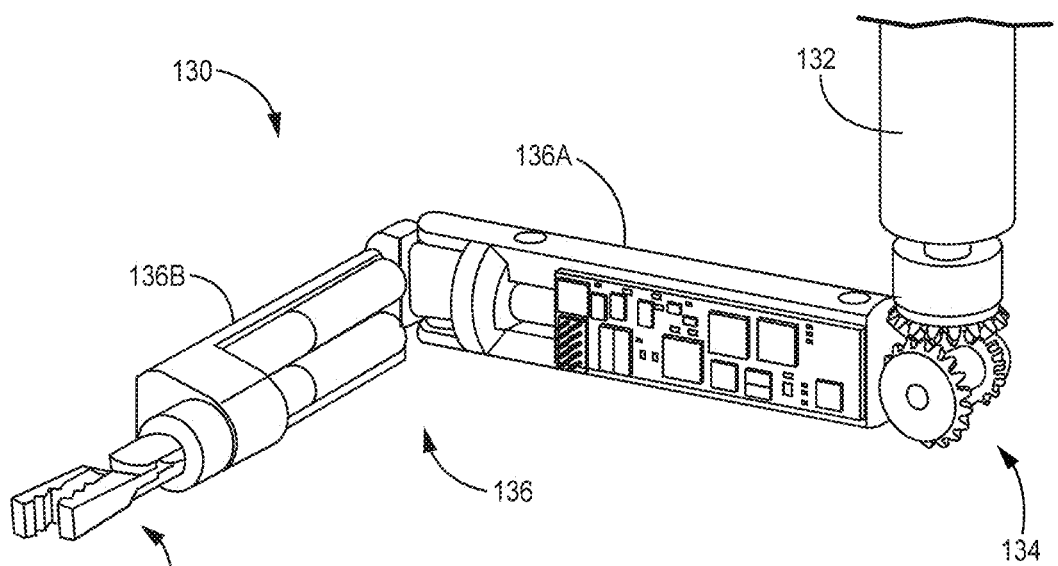
FIG. 4
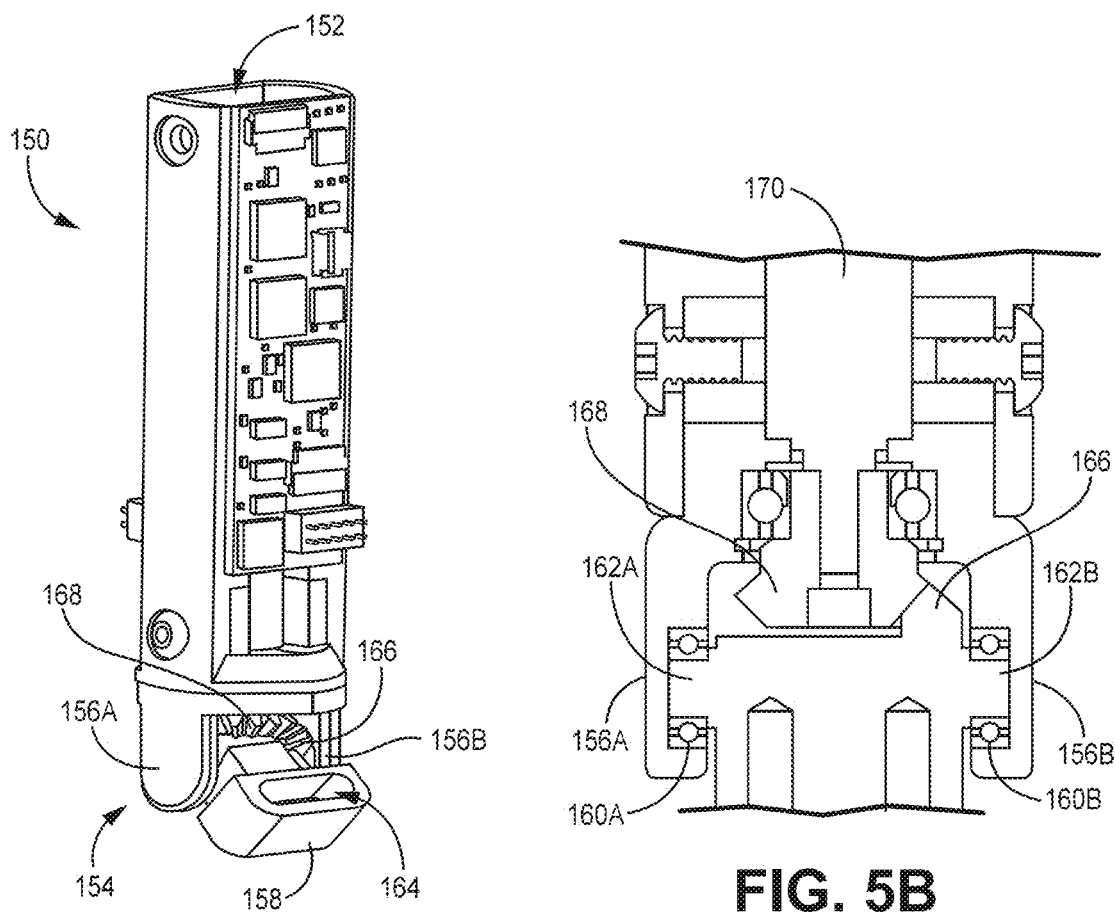
FIG. 5A
FIG. 5B

SINGLE-ARM ROBOTIC DEVICE WITH COMPACT JOINT DESIGN AND RELATED SYSTEMS AND METHODS

CROSS-REFERENCE TO RELATED APPLICATION(S)

This application claims priority as a continuation of U.S. application Ser. No. 17/980,665, filed Nov. 4, 2022, and entitled "Single-Arm Robotic Device with Compact Joint Design and Related Systems and Methods," which claims priority as a continuation of U.S. application Ser. No. 17/236,489, filed Apr. 21, 2021 and entitled "Single-Manipulator Robotic Device with Compact Joint Design and Related Systems and Methods," which issued as U.S. Pat. No. 11,504,196 on Nov. 22, 2022, which claims priority as a continuation of U.S. application Ser. No. 16/241,263, filed Jan. 7, 2019 and entitled "Single-Manipulator Robotic Device with Compact Joint Design and Related Systems and Methods," which issued as U.S. Pat. No. 11,013,564 on May 25, 2021, which claims the benefit under 35 U.S.C. § 119(e) to U.S. Provisional Application 62/614,127, filed Jan. 5, 2018 and entitled "Single-Manipulator Robotic Device With Compact Joint Design," the disclosures of which are hereby incorporated herein by reference in their entireties.

GOVERNMENT SUPPORT

This invention was made with government support under Grant No. W81XWH-08-02-0043, awarded by the U.S. Army Medical Research and Materiel Command; and Grant No. W81XWH-09-2-0185, awarded by the U.S. Army Medical Research and Materiel Command. The government has certain rights in the invention.

FIELD OF THE INVENTION

The various embodiments herein relate to various medical devices and related components, including robotic and/or in vivo surgical devices and related components, such as arms and end effectors. More specifically, disclosed herein are robotic surgical devices and systems for use in minimally invasive surgical procedures.

BACKGROUND OF THE INVENTION

Advancements in minimally-invasive surgical (M.I.S.) techniques continue to combat the major drawbacks of open surgery, which include lengthy recovery times, increased chance of postoperative infection, distinct cosmetic remnants, and other such disadvantages. Minimally invasive laparoscopic surgery is one type of M.I.S. technique and consists of the insertion of thin profiled tools and accessories into a gas-inflated abdominal region, eliminating the need for a large incision. However, these procedures also have limitations, including increased duration of surgery, reduction in visibility of the surgical site, and greater dexterity requirements of the surgeon. Accordingly, robotic platform integration has been introduced to the surgical field of medicine and looks to challenge these limitations.

A more recent minimally-invasive laparoscopic surgical technique is Laparo-Endoscopic Single-Site Surgery (LESS) (also commonly referred to as Single-Incision Laparoscopic Surgery (SILS)), which allows for access through a single incision into the abdomen. In order to operate, the surgeon must cross the tools through the port, causing a loss of triangulation, referred to as the "chopsticks effect." This process has also included, in some instances, a shift in the type of passageway or access point into the peritoneal cavity from the traditional trocar to a single-port entry device.

While single-port entry systems for use in LESS/SILS procedures are currently insubstantial, one device that has gained popularity is the GelPort® (hereafter referred to as "GelPort") system, which has been adapted to work as a passageway for trocars and robotic platforms.

By comparison, a traditional trocar is a relatively simple device that includes two known components: an outer sleeve (or "cannula") and an obturator. The tube-like cannula acts as the actual passageway into the abdomen, while the obturator is the component with the generally sharp distal end that is positioned through the cannula and creates the passageway into the peritoneal cavity via the skin of the patient.

The industry standard in externally-actuated surgical robotic platforms is the Da Vinci® Surgical System (hereafter referred to as "Da Vinci"), which consists of a master-slave configuration in which the surgeon(s) operates from a remote console. Da Vinci is also capable of performing single-site surgery. Disadvantages of Da Vinci include cost (the system costs millions of dollars, making it unaffordable for smaller less funded hospitals), having a large base that takes up a good portion of the area surrounding the operating bed (as well as various additional consoles scattered throughout the operating room), and being a highly complex system that requires extensive training and experience before a surgeon can operate on a human.

There is a need in the art for an improved robotic surgical system.

BRIEF SUMMARY OF THE INVENTION

Discussed herein are various single-armed robotic device embodiments with in-line shoulder joints.

In Example 1, a robotic device comprises a first elongate device body comprising first and second motors, a second elongate device body coupled to a distal end of the first elongate device body, a first driveshaft disposed through the second elongate device body and operably coupled to the first motor, a second driveshaft disposed through the second elongate device body and operably coupled to the second motor, the second driveshaft operably coupled at a distal end to a first bevel gear, a shoulder joint, and an arm operably coupled to the output body. The shoulder joint comprises a differential yoke rotationally coupled to the first driveshaft, a dual shaft rotatably disposed within the yoke lumen, and an output body rotatably disposed over the extension shaft. The differential yoke comprises a yoke body and a yoke lumen defined in the differential yoke, wherein the lumen has a longitudinal axis that is transverse to the longitudinal axis of the body. In addition, the dual shaft comprises a rotational shaft rotatably disposed within the yoke lumen, the rotational shaft rotationally coupled to the first bevel gear, and an extension shaft extending from the rotational shaft such that a longitudinal axis of the extension shaft is transverse to a longitudinal axis of the rotational shaft.

Example 2 relates to the robotic device according to Example 1, wherein the first driveshaft is rotatably disposed within and being radially concentric with the second driveshaft.

Example 3 relates to the robotic device according to Example 1, further comprising a third driveshaft operably coupled to a third motor, the third driveshaft operably coupled at a distal end to a second bevel gear, wherein the second bevel gear is operably coupled to the output body.

Example 4 relates to the robotic device according to Example 3, wherein the first driveshaft is rotatably disposed within and being radially concentric with the third driveshaft, and wherein the third driveshaft is rotatably disposed within and being radially concentric with the second driveshaft.

Example 5 relates to the robotic device according to Example 1, wherein the device has no second arm.

Example 6 relates to the robotic device according to Example 1, wherein the shoulder joint is a unitary shoulder joint.

Example 7 relates to the robotic device according to Example 1, wherein the second elongate device body has a cross-sectional diameter that is less than a cross-sectional diameter of the first elongate device body.

Example 8 relates to the robotic device according to Example 1, wherein the second elongate device body is sized and structured to be positionable through a standard trocar port.

Example 9 relates to the robotic device according to Example 1, wherein the shoulder joint is an in-line joint that is collinear with the second elongate device body.

In Example 10, a robotic device comprises a first elongate device body comprising first, second, and third motors disposed within the first elongate device body, a second elongate device body coupled to a distal end of the first elongate device body, a first driveshaft disposed through the second elongate device body and operably coupled to the first motor, a second driveshaft disposed through the second elongate device body and operably coupled to the second motor, the second driveshaft operably coupled at a distal end to a first bevel gear, a third driveshaft disposed through the second elongate device body and operably coupled to the third motor, the third driveshaft operably coupled at a distal end to a second bevel gear, a shoulder joint, and an arm operably coupled to the output body. The shoulder joint comprises a differential yoke rotationally coupled to the first driveshaft, a T shaft rotatably disposed within the yoke lumen, and an output body rotatably disposed over the extension shaft, the output body rotationally coupled to the first bevel gear. The differential yoke comprises a yoke body and a yoke lumen defined in the differential yoke, wherein the yoke lumen has a longitudinal axis that is transverse to the longitudinal axis of the body. The T shaft comprises a rotational shaft rotatably disposed within the yoke lumen, the rotational shaft rotationally coupled to the second bevel gear, and an extension shaft extending from the rotational shaft.

Example 11 relates to the robotic device according to Example 10, wherein the first driveshaft is rotatably disposed within and radially concentric with the second driveshaft, and wherein the second driveshaft is rotatably disposed within and radially concentric with the third driveshaft.

Example 12 relates to the robotic device according to Example 10, wherein the yoke lumen is defined by opposing first and second yoke lumen walls, the first yoke lumen wall comprising a first slot and the second yoke lumen wall comprising a second slot.

Example 13 relates to the robotic device according to Example 12, wherein the extension shaft is disposable within the first and second slots.

Example 14 relates to the robotic device according to Example 10, wherein a longitudinal axis of the extension shaft is transverse to a longitudinal axis of the rotational shaft.

Example 15 relates to the robotic device according to Example 10, wherein the first elongate device body has a cross-sectional diameter that is greater than a cross-sectional diameter of the second elongate device body.

Example 16 relates to the robotic device according to Example 10, wherein the arm comprises an upper arm body; a forearm body; an elbow joint coupling the forearm body to the upper arm body; an end effector; and a wrist joint coupling the end effector to the forearm body, wherein the upper arm body is operably coupled to the output body.

In Example 17, a robotic device comprises a first elongate device body comprising first, second, and third motors disposed within the first elongate device body, a second elongate device body coupled to a distal end of the first elongate device body, a first driveshaft disposed through the second elongate device body and operably coupled to the first motor, a second driveshaft disposed through the second elongate device body and operably coupled to the second motor, a third driveshaft disposed through the second elongate device body and operably coupled to the third motor, a shoulder joint, and an arm operably coupled to the output body. The second driveshaft is operably coupled at a distal end to a first bevel gear, wherein the first driveshaft is rotatably disposed within and radially concentric with the second driveshaft. The third driveshaft is operably coupled at a distal end to a second bevel gear, wherein the second driveshaft is rotatably disposed within and radially concentric with the third driveshaft. The shoulder joint comprises a differential yoke rotationally coupled to the first driveshaft, a T shaft rotatably disposed within the yoke lumen, and an output body rotatably disposed over the extension shaft, the output body rotationally coupled to the first bevel gear. The differential yoke comprises a yoke body and a yoke lumen defined in the differential yoke by opposing first and second curved shells, wherein the first curved shell comprises a first slot and the second curved shell comprises a second slot, and wherein the yoke lumen has a longitudinal axis that is transverse to the longitudinal axis of the body. The T shaft comprises a rotational shaft rotatably disposed within the yoke lumen, the rotational shaft rotationally coupled to the second bevel gear, and an extension shaft extending from the rotational shaft.

Example 18 relates to the robotic device according to Example 17, wherein the extension shaft is disposable within the first and second slots.

Example 19 relates to the robotic device according to Example 17, wherein the first elongate device body has a cross-sectional diameter that is greater than a cross-sectional diameter of the second elongate device body.

Example 20 relates to the robotic device according to Example 17, wherein the shoulder joint has a cross-sectional diameter that is less than or substantially similar to a cross-sectional diameter of the second elongate body.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 1A is a perspective view of a single-armed robotic device disposed through a trocar port, according to one embodiment.

FIG. 1B is a side view of the robotic device of FIG. 1A, according to one embodiment.

FIG. 1C is a top view of the robotic device of FIG. 1A, according to one embodiment.

FIG. 4 is a perspective view of a robotic arm and a portion of a second elongate body of a single-armed robotic device, according to one embodiment.

FIG. 5A is a side view of an upper arm of a robotic arm of a robotic device, according to one embodiment.

FIG. 5B is a cross-sectional cutaway side view of the elbow joint of the robotic arm of FIG. 5A, according to one embodiment.

DETAILED DESCRIPTION

Figure 2A:
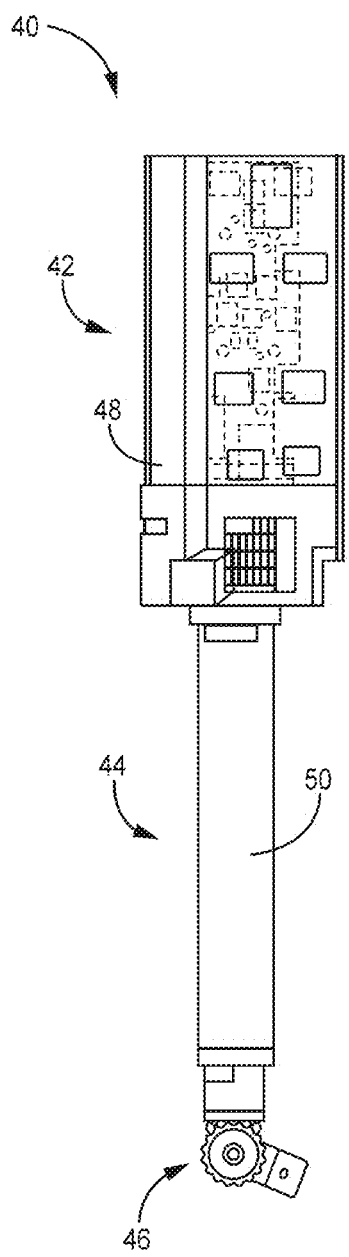
FIG. 2A is a side view of the first and second elongate bodies of a robotic device, according to one embodiment.

The various robotic surgical device and system embodiments disclosed or contemplated herein include a robotic device having an elongate body having a minimal cross-sectional profile and a single robotic arm attached thereto via an in-line shoulder joint.

It is understood that the various implementations of robotic devices and related methods and systems disclosed herein can be incorporated into or used with any other known medical devices, systems, and methods. For example, the various implementations disclosed herein may be incorporated into or used with any of the medical devices and systems disclosed in U.S. Pat. No. 7,492,116 (filed on Oct. 31, 2007 and entitled "Robot for Surgical Applications"), U.S. Pat. No. 7,772,796 (filed on Apr. 3, 2007 and entitled "Robot for Surgical Applications"), U.S. Pat. No. 8,179,073 (issued May 15, 2011, and entitled "Robotic Devices with Agent Delivery Components and Related Methods"), U.S. Pat. No. 8,343,171 (issued Jan. 1, 2013 and entitled "Methods and Systems of Actuation in Robotic Devices"), U.S. Pat. No. 8,679,096 (issued Mar. 25, 2014 and entitled "Multifunctional Operational Component for Robotic Devices"), U.S. Pat. No. 8,828,024 (issued on Sep. 9, 2014 and entitled "Methods and Systems of Actuation in Robotic Devices"), U.S. Pat. No. 8,834,488 (issued Sep. 16, 2014 and entitled "Magnetically Coupleable Surgical Robotic Devices and Related Methods"), U.S. Pat. No. 8,894,633 (issued Nov. 25, 2014 and entitled "Modular and Cooperative Medical Devices and Related Systems and Methods"), U.S. Pat. No. 8,968,267 (issued Mar. 3, 2015 and entitled "Methods and Systems for Handling or Delivering Materials for Natural Orifice Surgery"), U.S. Pat. No. 8,968,332 (issued Mar. 3, 2015 and entitled "Magnetically Coupleable Robotic Devices and Related Methods"), U.S. Pat. No. 8,974,440 (issued Mar. 10, 2015 and entitled "Modular and Cooperative Medical Devices and Related Systems and Methods"), U.S. Pat. No. 9,010,214 (Apr. 21, 2015 and entitled "Local Control Robotic Surgical Devices and Related Methods"), U.S. Pat. No. 9,060,781 (issued Jun. 23, 2015 and entitled "Methods, Systems, and Devices Relating to Surgical End Effectors"), U.S. Pat. No. 9,089,353 (issued Jul. 28, 2015 and entitled "Robotic Surgical Devices, Systems, and Related Methods"), U.S. Pat. No. 9,179,981 (issued on Nov. 10, 2015 and entitled "Multifunctional Operational Component for Robotic Devices"), U.S. Pat. No. 9,498,292 (issued Nov. 22, 2016 and entitled "Single Site Robotic Devices and Related Systems and Methods"), U.S. Pat. No. 9,579,088 (issued Feb. 28, 2017 and entitled "Methods, Systems, and Devices for Surgical Visualization and Device Manipulation"), U.S. Pat. No. 9,743,987 (Aug. 29, 2017 and entitled "Methods, Systems, and Devices Relating to Robotic Surgical Devices, End Effectors, and Controllers"), U.S. Pat. No. 9,770,305 (issued Sep. 26, 2017 and entitled "Robotic Surgical Devices, Systems, and Related Methods"), and U.S. Pat. No. 9,888,966 (issued Feb. 13, 2018 and entitled "Methods, Systems, and Devices Relating to Force Control Surgical Systems), all of which are hereby incorporated herein by reference in their entireties.

Further, the various implementations disclosed herein may be incorporated into or used with any of the medical devices and systems disclosed in copending U.S. Published Applications 2014/0046340 (filed Mar. 15, 2013 and entitled "Robotic Surgical Devices, Systems, and Related Methods"), 2014/0058205 (filed Jan. 10, 2013 and entitled "Methods, Systems, and Devices for Surgical Access and Insertion"), 2014/0303434 (filed Mar. 14, 2014 and entitled "Robotic Surgical Devices, Systems, and Related Methods"), 2015/0051446 (filed Jul. 17, 2014 and entitled "Robotic Surgical Devices, Systems, and Related Methods"), 2016/0074120 (filed Sep. 14, 2015, and entitled "Quick-Release End Effectors and Related Systems and Methods"), 2016/0135898 (filed Nov. 11, 2015 entitled "Robotic Device with Compact Joint Design and Related Systems and Methods"), 2016/0157709 (filed Feb. 8, 2016 and entitled "Medical Inflation, Attachment, and Delivery Devices and Related Methods"), 2017/0035526 (filed Aug. 3, 2016 and entitled "Robotic Surgical Devices, Systems, and Related Methods"), 2017/0354470 (filed May 18, 2017 and entitled "Robotic Surgical Devices, Systems, and Related Methods"), 2018/0055584 (filed Aug. 30, 2017 and entitled "Robotic Device with Compact Joint Design and an Additional Degree of Freedom and Related Systems and Methods"), 2018/0056527 (filed Aug. 25, 2017 and entitled "Quick-Release End Effector Tool Interface"), 2018/0140377 (filed Nov. 22, 2017 and entitled "Gross Positioning Device and Related Systems and Methods"), 2018/0147019 (filed Nov. 29, 2017 and entitled "User Controller with User Presence Detection and Related Systems and Methods"), and 2018/0161122 (filed Dec. 14, 2017 and entitled "Releasable Attachment Device for Coupling to Medical Devices and Related Systems and Methods"), all of which are hereby incorporated herein by reference in their entireties. In addition, the various implementations disclosed herein may be incorporated into or used with any of the medical devices and systems disclosed in copending U.S. application Ser. No. 16/144,807 (filed Sep. 27, 2018), which is hereby incorporated herein by reference in its entirety.

Certain device and system implementations disclosed in the patents and/or applications listed above can be positioned within a body cavity of a patient in combination with a support component similar to those disclosed herein and/or in certain of the patents and/or applications incorporated by reference above. An "in vivo device" as used herein means any device that can be positioned, operated, or controlled at least in part by a user while being positioned within a body cavity of a patient, including any device that is disposed through an opening or orifice of the body cavity and is coupled to a support component such as a rod or other such component, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain implementations provide for insertion of the present invention into the cavity while maintaining sufficient insufflation of the cavity. Further implementations minimize the physical contact of the surgeon or surgical users with the present invention during the insertion process. Other implementations enhance the safety of the insertion process for the patient and the present invention. For example, some implementations provide visualization of the present invention as it is being inserted into the patient's cavity to ensure that no damaging contact occurs between the system/device and the patient. In addition, certain implementations allow for minimization of the incision size/length. Further implementations reduce the complexity of the access/insertion procedure and/or the steps required for the procedure. Other implementations relate to devices that have minimal profiles, minimal size, or are generally minimal in function and appearance to enhance ease of handling and use.

As in manual laparoscopic procedures, a known insufflation system can be used to pump sterile carbon dioxide (or other gas) into the patient's abdominal cavity. This lifts the abdominal wall from the organs and creates space for the robot. In certain implementations, the system has no direct interface with the insufflation system. Alternatively, the system can have a direct interface to the insufflation system.

According to various embodiments, the insertion port is a traditional trocar or a modified trocar as described elsewhere herein. In such implementations, the device embodiments herein—or a portion thereof—are disposed through the cannula of the trocar in a fashion described in more detail below. Alternatively, in certain implementations, the insertion port is single-port entry device that is a known, commercially-available flexible membrane placed transabdominally to seal and protect the abdominal incision. One example of such a single-port entry device is the GelPort® discussed above. This off-the-shelf component is the same device used in the same way for Hand-Assisted Laparoscopic Surgery (HALS). The only difference is that the working arms of the robot are inserted into the abdominal cavity through the insertion port rather than the surgeon's hand. The robot body seals against the insertion port, thereby maintaining insufflation pressure. The port is single-use and disposable. In a further alternative, any known port can be used.

Certain implementations disclosed herein relate to "combination" or "modular" medical devices that can be assembled in a variety of configurations. For purposes of this application, both "combination device" and "modular device" shall mean any medical device having modular or interchangeable components that can be arranged in a variety of different configurations, and the related systems. The modular components and combination devices disclosed herein also include segmented triangular or quadrangular-shaped combination devices. These devices, which are made up of modular components (also referred to herein as "segments") that are connected to create the triangular or quadrangular configuration, can provide leverage and/or stability during use while also providing for substantial payload space within the device that can be used for larger components or more operational components. As with the various combination devices disclosed and discussed above, according to one implementation these triangular or quadrangular devices can be positioned inside the body cavity of a patient in the same fashion as those devices discussed and disclosed above.

The various system implementations described herein are used to perform robotic surgery. Further, the various implementations disclosed herein can be used in a minimally invasive approach to a variety of procedures that are typically performed "open" by known technologies, with the potential to improve clinical outcomes and health care costs, including, for example, general surgery applications in the abdominal cavity, such as, for example, colon resection and other known procedures. Further, the various implementations disclosed herein can be used in place of the known mainframe-like laparoscopic surgical robots that reach into the body from outside the patient. That is, the less-invasive robotic systems, methods, and devices according to the implementations disclosed herein feature small, self-contained surgical devices that are inserted in their entireties through a single incision in the patient's abdomen. Designed to utilize existing tools and techniques familiar to surgeons, the devices disclosed herein will not require a dedicated operating room or specialized infrastructure, and, because of their much smaller size, are expected to be significantly less expensive than existing robotic alternatives for laparoscopic surgery. Due to these technological advances, the various implementations herein could enable a minimally invasive approach to procedures performed in open surgery today. In certain implementations, the various systems described herein are based on and/or utilize techniques used in manual laparoscopic surgery including insufflation of the abdominal cavity and the use of ports to insert tools into the abdominal cavity.

As will be described in additional detail below, components of the various system implementations disclosed or contemplated herein can include a control console and a robot having a minimal cross-sectional profile and a single robotic arm as described herein. The robot implementations are constructed and arranged to be inserted into the insufflated abdominal cavity as described in further detail herein.

While the various embodiments herein are described as having motors, it is understood that any type of known actuators can be used in place of the motors. Further, while the transmission components that transmit the force from the motors within the device are described as shafts that are coupled via gears, it is understood that any type of transmission components or mechanisms can be incorporated herein in place of such shafts and gears, including hydraulic or pneumatic components or other mechanical components such as cables and pulleys or similar components.

The various implementations are disclosed in additional detail in the attached figures and the related discussion thereof, as set forth herein.

FIGS. 1A-1C depict one embodiment of the single manipulator device (also referred to herein as the "unitary manipulator," "single arm," "unitary arm," "in-line joint," "in-line shoulder joint," and "robotic surgical" device) 10 according to one embodiment. In this implementation, the device 10 has a first body (also referred to herein as an "external body" or "first support beam") 12, a second body (also referred to herein as an "internal body" or "second support beam") 14, a first arm component (also referred to herein as an "upper arm") 16, a second arm component (also referred to herein as a "forearm") 18, and an operational component (also referred to herein as an "end effector") 20. In this embodiment as depicted and various other implementations herein, the internal body 14 has a smaller cross-sectional diameter than the external body 12 such that the internal body 14 can be inserted through a smaller port than would be possible for the external body 12, including, for example, a trocar port such as the port 28 depicted in FIG. 1A. Note in FIG. 1A that the internal body 14 is disposed through and positioned within the trocar port 28 such that the distal end of the internal body 14 extends out of the distal end of the trocar cannula 30. As such, the distal end of the internal body 14 and the shoulder joint 22 are disposed within the internal target cavity of the patient. The second body 14 is coupled to the first body 12. In certain embodiments, the first and second bodies 12, 14 are removably coupled. Alternatively, the first and second bodies 12, 14 are fixedly coupled or are integral with each other as a single, unitary component. In a further alternative, the first and second bodies 12, 14 are moveably coupled to each other in a jointed or other non-rigid fashion.

The first arm component 16 is rotatably coupled to the second body 14 via a first joint (also referred to herein as a "shoulder joint") 22, while the second arm component 18 is rotatably coupled to the first arm component 16 via a third joint (also referred to herein as an "elbow joint") 24, and the operational component 20 is rotataby coupled to the second arm component 18 via a fourth joint (also referred to herein as a "wrist joint") 26. Each of these components will be discussed in further detail below, according to various embodiments of the robotic surgical device.

It is understood that the compact in-line (or "coaxial") shoulder joint as described in additional detail with respect to the various embodiments disclosed or contemplated herein presents a less-invasive approach to the insertable portion of the robot in comparison to devices having shoulder joints that are not in-line, including those devices having two shoulder joints. That is, the in-line shoulder joint implementations herein have a smaller cross-sectional diameter in comparison to the known non-in-line or double shoulder joints.

One embodiment of a single-armed device 40, and more specifically the external body 42, the internal body 44, and shoulder joint 46 thereof, is depicted in further detail in FIGS. 2A-2F. Like every other implementation disclosed or contemplated herein, this specific device 40 embodiment has a shoulder joint 46 with 3 degrees of freedom ("DOF") and a minimal cross-sectional diameter for ease of insertion through trocars and other insertion devices. The minimal diameter is accomplished via the specific design of the various components within the internal body 44 and the joint 46, as described in further detail below.

FIG. 2A depicts a side view of the device 40, including the external body 42, the internal body 44, and the shoulder joint 46. More specifically, the figure shows the external casing or housing 48 of the external body 42 and the external casing or housing 50 of the internal body 44.

Figure 2B:
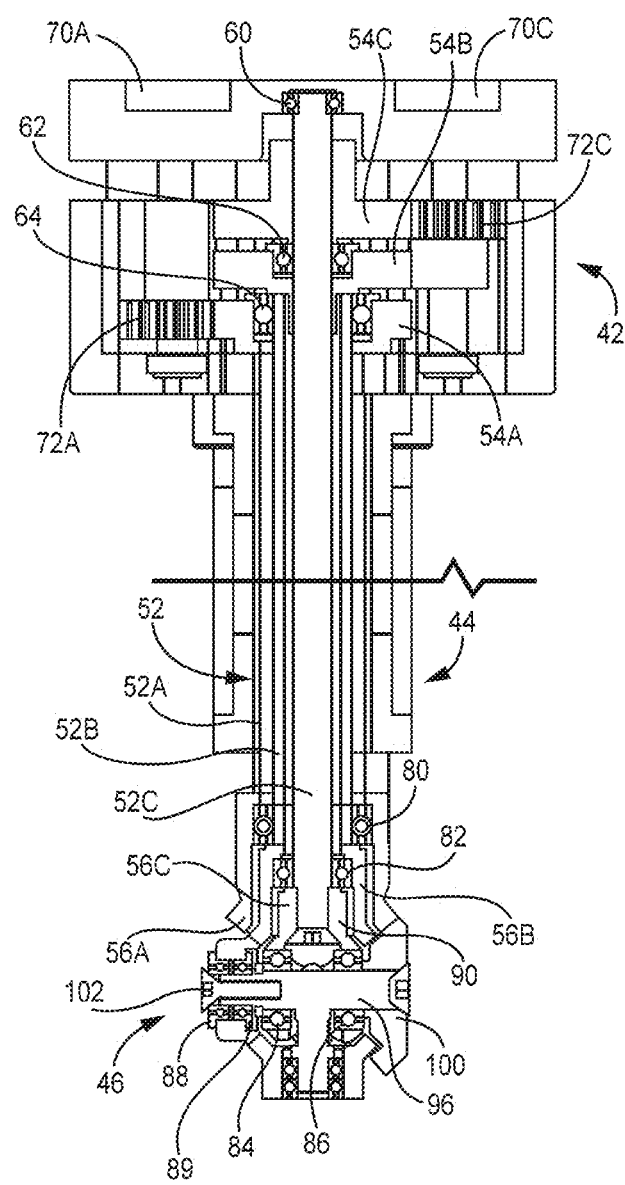
FIG. 2B is a cross-sectional cutaway side view of a portion of the first and second elongate bodies of the robotic device of FIG. 2A, according to one embodiment.

FIG. 2B depicts a cross-sectional front view of the external body 42, the internal body 44, and the shoulder joint 46 in which certain internal components of those components are visible, according to one exemplary embodiment. In this implementation and other embodiments disclosed or contemplated herein, the external body 42 contains the actuators (which, in this specific embodiment are motors) 70A, 70B, 70C that actuate the shoulder joint 46 via the transmission shafts (also referred to herein as "nested driveshafts") 52 disposed within the internal body 44. This configuration (with the motors 70A, 70B, 70C disposed within the external body 42 and the nested driveshafts 52 disposed in a nested configuration within the internal body 44 makes it possible for the internal body 44 to have a smaller cross-sectional diameter than the external body 42, as discussed above with respect to device 10. The set of nested driveshafts 52 are rotatably disposed within the internal body 44. As set forth herein, the word "nested" is intended to describe components that are concentric such that at least one of the components is positioned inside another of those components and each of the components have a common axis of rotation.

With respect to FIG. 2B, the set of nested driveshafts 52 is made up of a first or outer driveshaft 52A, a second or middle driveshaft 52B, and a third or inner driveshaft 52C. The set of nested driveshafts 52 extend from the external body 42 into and through the internal body 44 as shown. The inner driveshaft 52C is rotatably disposed within the middle driveshaft 52B as shown, and has a driven gear 54C fixedly or integrally attached at its proximal end. At its distal end, the inner driveshaft 52C is coupled to or integral with a differential yoke (also referred to herein as a "shoulder housing" or "conversion body") 56C. The middle driveshaft 52B is rotatably disposed within the outer driveshaft 52A as shown, and has a driven gear 54B fixedly or integrally attached at its proximal end. At its distal end, the middle driveshaft 52B is coupled to a second or inner drive bevel gear 56B. The outer driveshaft 52A is rotatably disposed within the internal body 44 and has a driven gear 54A fixedly or integrally attached at its proximal end. At its distal end, the outer driveshaft 52A is coupled to a first or outer drive bevel gear 56A.

Figure 2C:
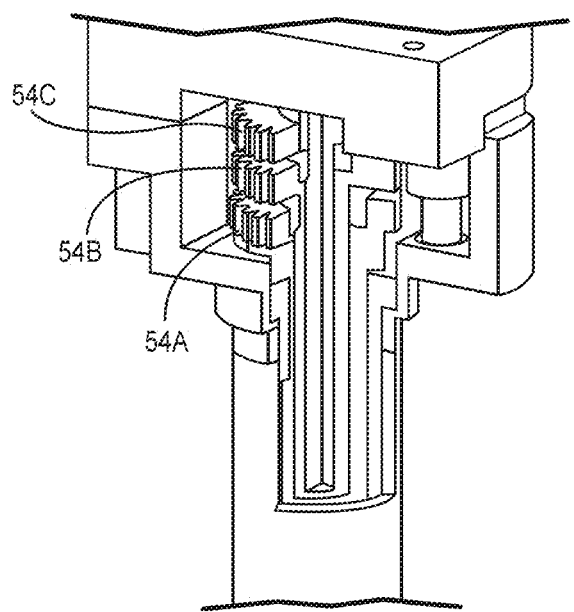
FIG. 2C is a cross-sectional, partial cutaway perspective view of an expanded portion of the first and second elongate bodies of the robotic device of FIG. 2A, according to one embodiment.

Various internal components at the proximal end of the internal body 44 and distal end of the external body 42 are best depicted in FIGS. 2B and 2C, including the proximal end of the driveshafts 52A, 52B, 52C and related gears and motors that drive those driveshafts 52A, 52B, 52C, according to one embodiment. As best shown in FIG. 2B, the proximal end of the inner driveshaft 52C is rotatably supported in the external body 42 via a first shaft bearing 60 and a second shaft bearing 62. Further, the proximal end of the middle driveshaft 52B, including the driven gear 54B, is rotatably supported in the external body 42 via the second shaft bearing 62 and a third shaft bearing 64. In addition, the proximal end of the outer driveshaft 52A, including driven gear 54A, is rotatably supported in the external body 42 via the third shaft bearing 64.

As best shown in FIGS. 2B and 2C, the set of nested driveshafts 52 has three motors operably coupled thereto (although only two of the three motors are visible), wherein the three motors are disposed within the external body 42 as discussed above. More specifically, motor 70A has a motor drive gear 72A that is coupled to the driven gear 54A (which is coupled to the outer driveshaft 52A). Further, motor 70C has a motor drive gear 72C that is coupled to the driven gear 54C (which is coupled to the inner driveshaft 52C). In addition, a third motor (logically identified as 70B but not visible in the figures due to the perspective thereof) has a third motor drive gear (logically identified as 72B but also not visible) that is coupled to the driven gear 54B (which is coupled to the middle driveshaft 52B). The positioning and functionality of the third motor and third motor drive gear are understood by one of ordinary skill in the art based on the description herein.

In one embodiment, the motors 70A, 70B, 70C are 12 volt Faulhaber 1226 series brushless DC motors coupled to Faulhaber 256:1 planetary gearboxes with an efficiency rating of 0.60. Alternatively, any known motors can be used in the external body 42.

Thus, in operation, the motor 70A can be actuated to drive rotation of the outer driveshaft 52A by driving rotation of motor drive gear 72A, which drives rotation of the driven gear 54A. Similarly, the motor 70B (not visible in the figures) can be actuated to drive rotation of the middle driveshaft 52B by driving rotation of motor drive gear 72B (also not visible), which drives rotation of the driven gear 54B. In a similar fashion, the motor 70C can be actuated to drive rotation of the inner driveshaft 52C by driving rotation of motor drive gear 72C, which drives rotation of the driven gear 54C.

Figure 2D:
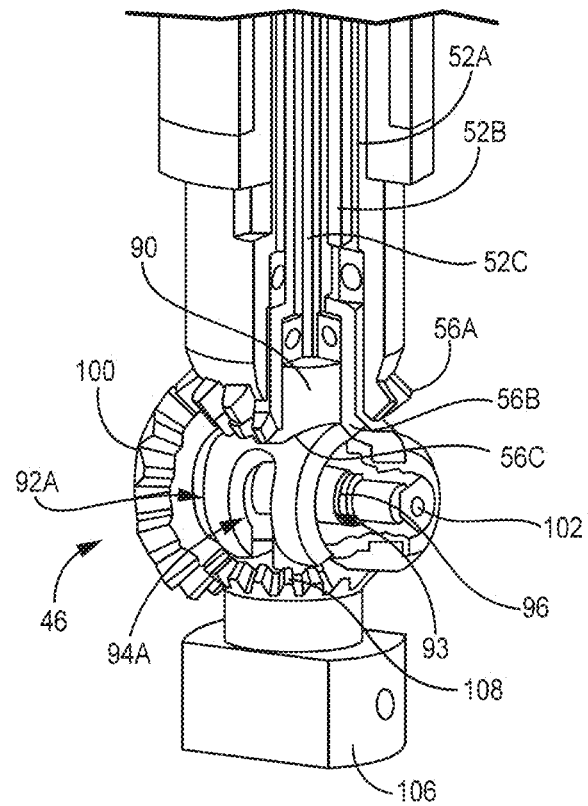
FIG. 2D is a cross-sectional, partial cutaway perspective view of an expanded portion of the second elongate body and shoulder joint of the robotic device of FIG. 2A, according to one embodiment.
Figure 2E:
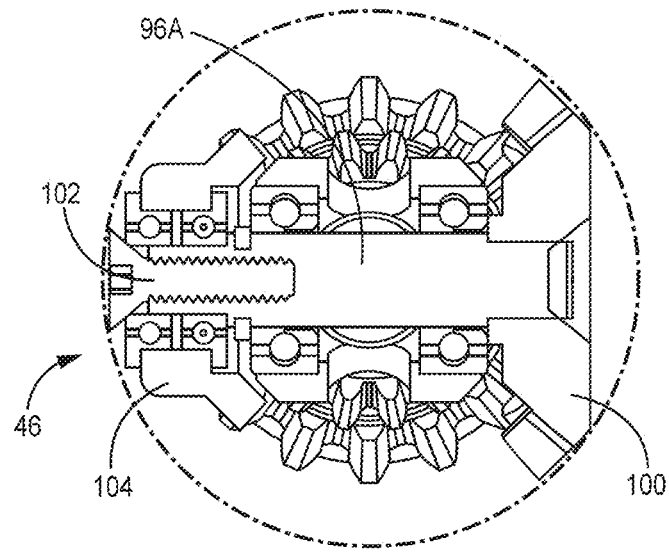
FIG. 2E is a cross-sectional cutaway bottom view of the shoulder joint of the robotic device of FIG. 2A, according to one embodiment.
Figure 2F:
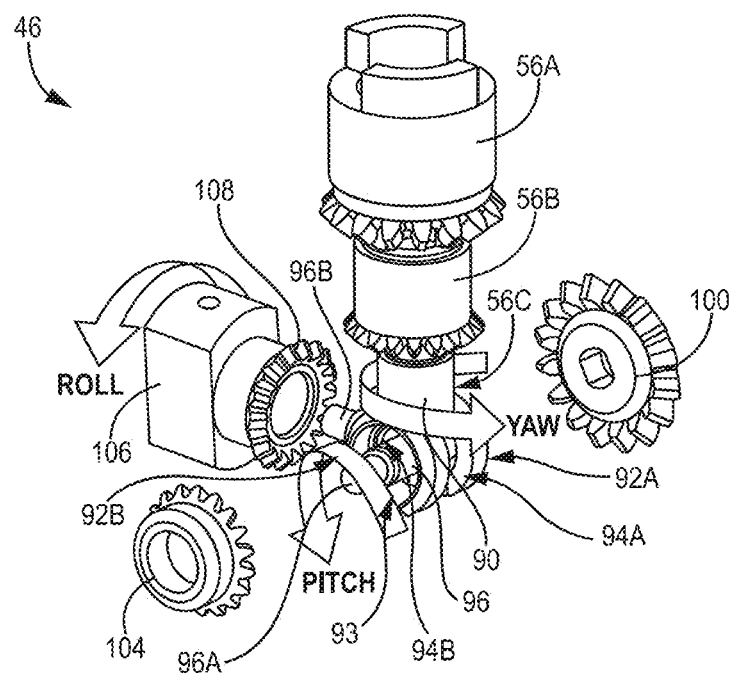
FIG. 2F is a exploded perspective view of the shoulder joint of the robotic device of FIG. 2A, according to one embodiment.

FIGS. 2B, 2D, 2E, and 2F depict the shoulder joint 46 and its various components, according to one implementation. More specifically, FIG. 2D depicts a cross-sectional perspective view of the internal components of the joint 46, while FIG. 2E depicts a cross-sectional top view of the joint 46, and FIG. 2F depicts an exploded view of the internal components of the joint 46. As discussed above, and as shown in FIGS. 2B, 2D, and 2F, the outer driveshaft 52A is coupled (or rotationally constrained) to the outer drive bevel gear 56A, while the middle driveshaft 52B is coupled to the inner drive bevel gear 56B, and the inner driveshaft 52C is coupled to the differential yoke 56C. As best shown in FIG. 2B, at the distal end, the outer driveshaft 52A and outer drive bevel gear 56A are supported by the first shoulder bearing 80. In addition, the middle driveshaft 52B and the inner drive bevel gear 56B are supported by the first shoulder bearing 80 and the second shoulder bearing 82.

As best shown in FIGS. 2D and 2F, the differential yoke 56C has a cylindrical body 90 and a yoke opening or partial lumen 93 defined at the distal end of the body 90. In one implementation as shown, the lumen 93 is defined by two opposing curved shells (or "curved walls") 92A, 92B that extend from the body 90 and define the yoke lumen 93 between the two shells 92A, 92B. In one embodiment, each of the two shells 92A, 92B is a set of two prongs, such that the first shell 92A is a first set of two curved prongs 92A and the second shell 92B is a second set of two curved prongs 92B. In addition, shaft slots 94A, 94B are defined in the two shells 92A, 92B. Thus, in those embodiments in which the shells 92A, 92B are prong pairs 92A, 92B, the shaft slots 94A, 94B are defined between each of two prongs of each set of prongs 92A, 92B. The cylindrical body 90 is disposed in the joint 46 such that its longitudinal axis is parallel to and concentric with the longitudinal axis of the internal body 44. In contrast, the yoke lumen 93 defined by the two shells 92A, 92B has a longitudinal axis that is transverse to the longitudinal axis of the cylindrical body 90.

Further, the joint 46 has a dual shaft (also referred to herein as a "t-bar" or "T shaft") 96 rotatably disposed within the yoke opening 93. The dual shaft 96 has a rotational shaft (also referred to as the "main shaft" or "pitch shaft") 96A and an extension shaft (also referred to as the "roll shaft") 96B. The extension shaft 96B has a longitudinal axis that is transverse to the longitudinal axis of the rotational shaft 96A. The pitch shaft 96A is rotatably supported within the yoke opening 93 by the third 84 and fourth 86 shoulder bearings (as best shown in FIG. 2B)—along with the fifth 88 and sixth 89 shoulder bearings (also best shown in FIG. 2B)—such that the pitch shaft 96A rotates around a longitudinal axis that is transverse to the longitudinal axis of the internal body 44 (and thus also the longitudinal axes of the set of nested driveshafts 52). Further, the pitch shaft 96A is coupled or rotationally constrained to the first shoulder bevel gear 100 such that rotation of the first shoulder gear 100 causes rotation of the rotational shaft 96A. The first shoulder gear 100 is rotatably coupled to the outer drive bevel gear 56A such that rotation of the outer drive bevel gear 56A causes rotation of the first shoulder gear 100. The bevel gear 100, the pitch shaft 96A, and the bearings 84, 86, 88, 89 are coupled together and "preloaded" by the screw 102 that is coupled to the pitch shaft 96A. Alternatively, any known attachment component can be used to couple together and preload these components. As such, rotation of the motor 70A causes rotation of the rotational shaft 96A and thus causes movement of the extension shaft 96B around the longitudinal axis of the rotational shaft 96A as described in additional detail below.

Continuing with FIGS. 2B, 2D, and 2F, the extension shaft 96B is coupled to or integral with the rotational shaft 96A and extends radially from the rotational shaft 96A such that the longitudinal axis of the extension shaft 96B is transverse to the longitudinal axis of the rotational shaft 96A, thereby resulting in the T-shaped configuration of the T shaft 96. When the pitch shaft 96A is rotatably disposed within the yoke opening 93 as described above, the extension shaft 96B extends from the rotational shaft 96A as best shown in FIG. 2F such that the extension shaft 96B is disposed in either of the shaft slots 94A, 94B between the prong sets 92A, 92B depending on the rotational position of the rotational shaft 96A. That is, as the rotational shaft 96A rotates, the extension shaft 96B rotates around the longitudinal axis of the rotational shaft 96A along a path that includes the two shaft slots 94A, 94B such that the extension shaft 96B can rotate at least 180° around the rotational shaft 96A.

Continuing with FIG. 2F, the shoulder joint 46 also has a second shoulder bevel gear 104 rotatably disposed on the end of the rotational shaft 96A opposite the first shoulder bevel gear 100 such that the second shoulder gear 104 can rotate in relation to the rotational shaft 96A. The second shoulder bevel gear 104 is rotatably coupled to the inner drive bevel gear 56B such that rotation of the inner drive bevel gear 56B causes rotation of the second shoulder bevel gear 104. Further, the second shoulder bevel gear 104 is also rotatably coupled to the output body (also referred to as the "roll body") bevel gear 108 such that rotation of the second shoulder gear 104 causes rotation of the output body bevel gear 108. As such, rotation of the inner drive bevel gear 56B causes rotation of the output body 106, as described in additional detail below.

The output body 106 with the output body bevel gear 108 is rotatably disposed on the extension shaft 96B such that the output gear 108 and body 106 can rotate in relation to the extension shaft 96B. Thus, rotation of the output body bevel gear 108 around the extension shaft 96B caused by rotation of the second shoulder bevel gear 104 also causes rotation of the output body 106. Further, rotation of the extension shaft 96B around the rotational axis of the rotational shaft 96A causes both the extension shaft 96B and the output body 106 disposed thereon to also rotate around the rotational axis of the shaft 96A, thereby resulting in the pitch motion of the arm attached thereto (such as arm 130 or upper arm 150, for example).

In use, the outer drive bevel gear 56A is rotatably coupled to the first shoulder bevel gear 100 as discussed above such that rotation of the outer drive bevel gear 56A causes rotation of the first shoulder bevel gear 100. This rotation of the first shoulder bevel gear 100 causes rotation of the rotational shaft 96A, which causes the movement of the extension shaft 96B—and the output body 106 coupled thereto—radially around the longitudinal axis of the rotational shaft 96A, which results in pitch.

Further, the inner drive bevel gear 56B is rotatably coupled to the second shoulder bevel gear 104 as discussed above such that the rotation of the inner drive bevel gear 56B causes rotation of the second shoulder bevel gear 104. This rotation of the second shoulder bevel gear 104 causes rotation of the output body bevel gear 108, which causes rotation of the output body 106 around the extension shaft 96B, which results in roll.

In addition, the inner driveshaft 52C is coupled to—or integral with—the differential yoke 56C as discussed above such that rotation of the inner driveshaft 52C causes rotation of the differential yoke 56C, which results in yaw.

Thus, the shoulder joint 46 provides three degrees of freedom. The shoulder joint 46 configuration provides those three degrees of freedom while minimizing the cross-sectional size thereof. FIG. 2E depicts the greatest cross-sectional diameter of the shoulder joint 46, which is also the largest cross-sectional diameter of the internal components of the device 40 and any other device embodiment disclosed or contemplated herein. As such, according to certain implementations, the cross-sectional diameter of the second or internal body (such as internal body 44) is no greater (or not substantially greater) than the cross-sectional diameter of the shoulder joint (such as shoulder joint 46), as best shown by example in FIG. 2B. In one implementation, the shoulder joint 46 has a maximum diameter of about 15 mm, which means that the internal body 44, the shoulder joint 46, and the robotic arm (not shown) coupled thereto can be inserted through any trocar or other insertion device having a minimum internal diameter of about 15 mm.

Figure 3:
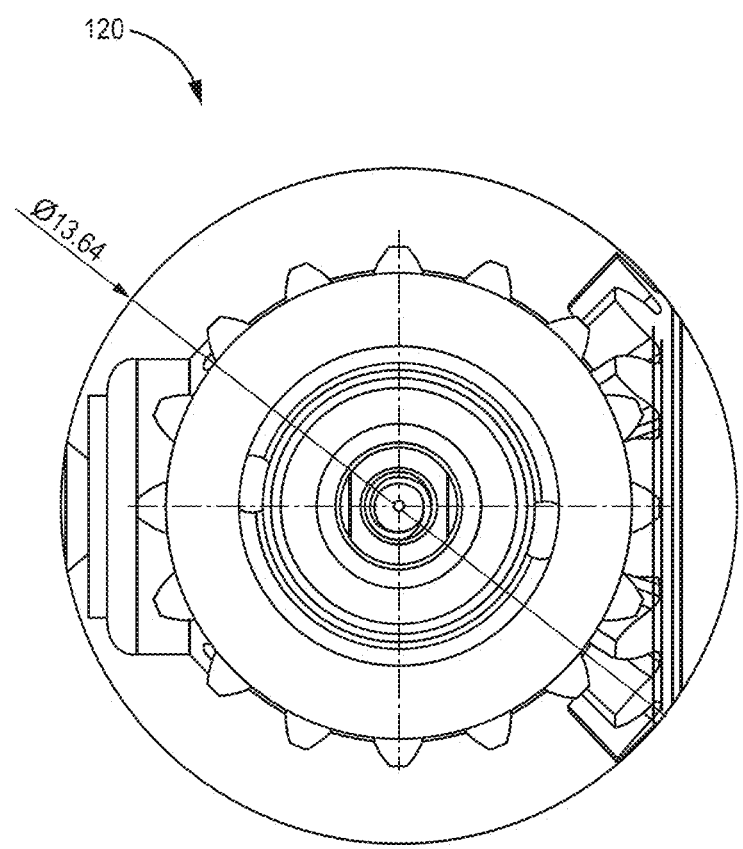
FIG. 3 is a cross-sectional cutaway top view of a shoulder joint of a robotic device, according to one embodiment.

FIG. 3 depicts yet another embodiment of a shoulder joint 120 with a similar configuration to the joint 46 discussed above and a maximum diameter of about 13.5 mm, meaning that any device embodiment having such a joint 120 can have an internal body, shoulder joint 120, and coupled robotic arm that can be inserted through any trocar or other insertion device having a minimum internal diameter of 13.5 mm.

Alternatively, any shoulder joint (such as joint 46 or 120) according to any embodiment disclosed or contemplated herein can have a maximum diameter ranging from about 13.5 mm to any desirable greater diameter. In a further embodiment, the maximum diameter of any such shoulder joint can be about 18 mm.

In the specific embodiments of FIGS. 1A-3 and the various other implementations disclosed or contemplated herein, one advantage of the in-line, three degree-of-freedom ("3 DOF") shoulder joint is the resulting reduced cross-sectional profile. That is, the entire device (such as device 40 or other such embodiments herein) has a smaller cross-sectional diameter (transverse to the longitudinal axes of the body and the single arm) in comparison to known devices having motors (and other such actuators) in the body thereof, including such known devices with two arms. The known two-armed devices have two arms attached to a single body such that the arms have mirrored, symmetric functionality. This known two-armed mirrored configuration results in a device with a larger cross-sectional profile. In contrast, the single-armed device embodiments disclosed or contemplated herein have smaller cross-sectional profiles and thus can be incorporated into a system of two or more such devices that allow for positioning the two or more devices in various locations into a patient's abdomen through various incisions at different locations therein. Given the variation in human anatomy across patients, the positioning of procedural tools and accessories can vary significantly by patient such that the use of separate single-armed devices can provide an advantage. Further, the use of two or more separate single-armed devices provides spatial and operational independence between the two or more robotic arms, thereby enabling independent gross positioning capabilities. As such, the device (such as device 40 or any other embodiment disclosed or contemplated herein) can be inserted through a smaller opening (such as a trocar port, other known port, or incision, for example) for use in a medical procedure, or two or more such devices can be inserted through two or more openings, thereby resulting in a less invasive procedure than the known devices.

Further, as discussed above, the in-line, 3 DOF shoulder joint embodiments herein (such as, for example, joints 46 or 120) have a maximum diameter that is smaller than most separate shoulder joints in the known two-armed devices. This reduced cross-sectional diameter results from the in-line shoulder joint configuration that consists of the combination of the differential yoke (such as yoke 16C) and the dual shaft (such as dual shaft 96) and how those two components are positioned with the various gears within the shoulder to result in a minimal diameter. Using the shoulder joint 46 as an example, the disposition of the rotatable dual shaft 96 within the differential yoke 16C in combination with (1) the rotatable coupling of the inner drive shaft 52C and the differential yoke 56C, and (2) the rotatable coupling of the outer drive bevel gear 56A with the first shoulder bevel gear 100 and thus with the rotational shaft 96A of the dual shaft 96 results in minimized profile of the shoulder joint 46. That is, unlike most known shoulder joints, the radially outermost component of the shoulder joint 46 is the first shoulder bevel gear 100. Put another way, the component driven by the first shoulder bevel gear 100 is disposed in an interior radial position in relation to the gear 100, rather than a position that is radially outside the gear 100 in relation to the cross-sectional midpoint of the shoulder 46. In contrast, in most known/prior shoulder joints, such an outer bevel gear would be coupled to a component disposed on the radially outer side of the bevel gear, thus resulting in a great cross-section diameter in comparison to the shoulder joints disclosed and contemplated herein.

The "in-line" or collinear feature of the 3 DOF shoulder joint 46 results from the differential yoke 56C—with the dual shaft 96 rotatably disposed therein—being rotationally coupled to the inner drive shaft 52C. Thus, when the dual shaft 96 is disposed such that the rotational shaft 96A extends away from the internal body 44 and is parallel and concentric with the longitudinal axis of the internal body 44 (such that an upper arm of a robotic arm (not shown) coupled thereto is also parallel and concentric with the longitudinal axis of the internal body 44), the rotation of the inner drive shaft 52C causes the directly corresponding rotation of the differential yoke 56C (and thus directly corresponding rotation of the upper arm attached thereto).

In certain embodiments, as best shown in FIG. 4, a single-arm device 130 similar to the embodiments above has an external body (not shown), an internal body 132, a shoulder joint 134, and a single robotic arm 136 coupled to the single shoulder joint 134. Further, in accordance with some implementations, the arm 136 has two components: a first arm component (also referred to herein as an "upper arm") 136A and a second arm component (also referred to herein as a "forearm") 136B. Further, some embodiments have an operational component (also referred to herein as an "end effector") 138 coupled to the arm 136.

FIGS. 5A and 5B depict one embodiment of an upper arm 150, according to one embodiment. This upper arm 150 embodiment can be fixedly coupled to the output body (such as output body 106 discussed above) of the joint (such as joint 46) such that the roll of the output body causes the upper arm 150 to rotate around its longitudinal axis. More specifically, the arm 150 has an opening 152 defined in its proximal end into which the output body (such as output body 106) can be disposed and thereby attached to the arm 150. Alternatively, any coupling mechanism, feature, or method can be used to couple the upper arm 150 to the output body.

The upper arm 150 also has an arm joint (also referred to herein as a "elbow joint") 154 at its distal end that allows for a jointed coupling to a forearm (such as forearm 180 as discussed below). The elbow joint 154 has two opposing supports (or "projections") 156A, 156B extending from or at the distal end of the upper arm 150 that define a space therebetween in which a coupling body 158 is rotatably disposed. Each of the supports 156A, 156B has a bearing 160A, 160B disposed on an inner wall thereof. The coupling body 158 has two rotational projections 162A, 162B, a coupling component 164, and a body bevel gear 166. The two rotational projections 162A, 162B, according to one implementation, are disposed within and rotatably coupled to the two bearings 160A, 160B, respectively, as best shown in FIG. 5B, such that the coupling body 158 can rotate in relation to the supports 156A, 156B. In this embodiment, the coupling component 164 is an opening 164 defined in the coupling body 158 that is configured to receive a portion of a forearm (such as forearm 180) such that the forearm portion is disposed within the opening 164 and the forearm is thereby coupled to the coupling body 158. Alternatively, the coupling component 164 can be any coupling mechanism, feature, or method can be used to couple the upper arm 150 to the forearm.

Further, the joint 154 includes an elbow joint bevel gear 168 that is coupled or rotationally constrained to an upper arm motor 170 such that actuation of the motor 170 causes rotation of the elbow joint bevel gear 168. The elbow joint bevel gear 168 is rotatably coupled to the body bevel gear 166 such that rotation of the elbow joint bevel gear 168 causes rotation of the body bevel gear 166, which thereby causes the coupling body 158 to rotate in relation to the supports 156A, 156B, thereby causing the forearm (such as forearm 180) coupled thereto to rotate in relation to the upper arm 150. Thus, actuation of the upper arm motor 170 can cause the forearm (such as forearm 180) to rotate in relation to the upper arm 150 at the elbow joint 154.

In one implementation, the upper arm 150 has additional space within the arm 150 (beyond the space occupied by the upper arm motor 170) to house additional components as necessary. For example, in one embodiment, one or more controllers (not shown) for controlling various components—including motors—of the arm or the robotic device can be disposed within the upper arm 150.

Figure 6A:
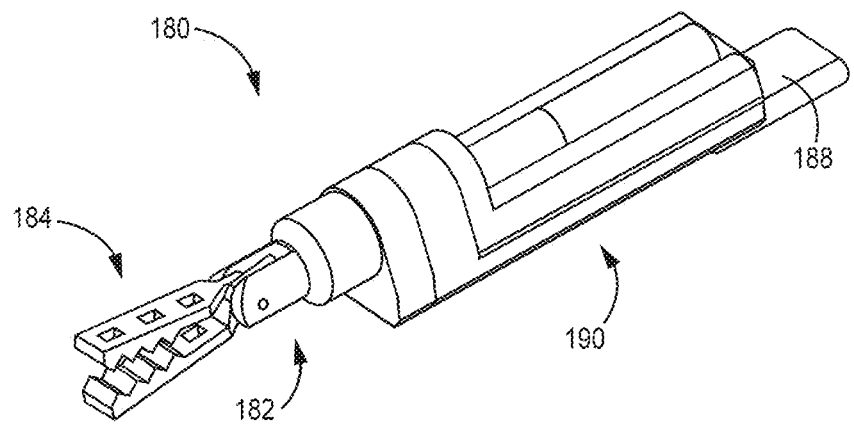
FIG. 6A is a perspective view of a forearm of a robotic arm, according to one embodiment.
Figures 6B, 6C:
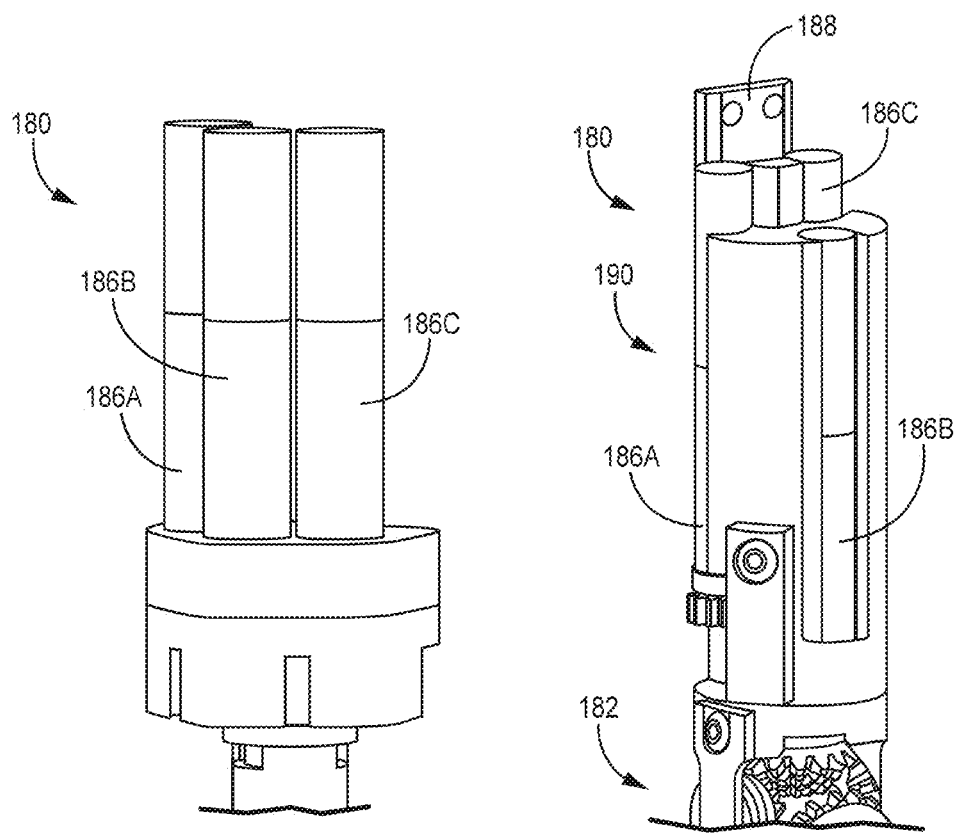
FIG. 6B is a cross-sectional, partial cutaway perspective view of an expanded portion of the forearm of FIG. 6A, according to one embodiment.
FIG. 6C is another cross-sectional, partial cutaway perspective view of an expanded portion of the forearm of FIG. 6A, according to one embodiment.

FIGS. 6A-6C depict one embodiment of an forearm 180, according to one embodiment. This forearm 180 embodiment can be fixedly coupled to the coupling component 164 of the coupling body 158 at the coupling projection 188 at the proximal end of the forearm 180. It is understood that any coupling mechanism or method can be used for this attachment.

The forearm 180 in this implementation has a wrist joint 182 at the distal end thereof, with an operational component ("end effector") 184 coupled to the wrist joint 182. In this specific embodiment, the end effector 184 is a grasper 184, but it is understood that the end effector 184 is removable and thus various known, interchangeable end effectors 184 can be used herewith. Further, as best shown in FIGS. 6B and 6C, the forearm 180 in this embodiment has three motors disposed within the body 190 of the forearm 180: the first motor 186A, the second motor 186B, and the third motor 186C.

Figure 7A:
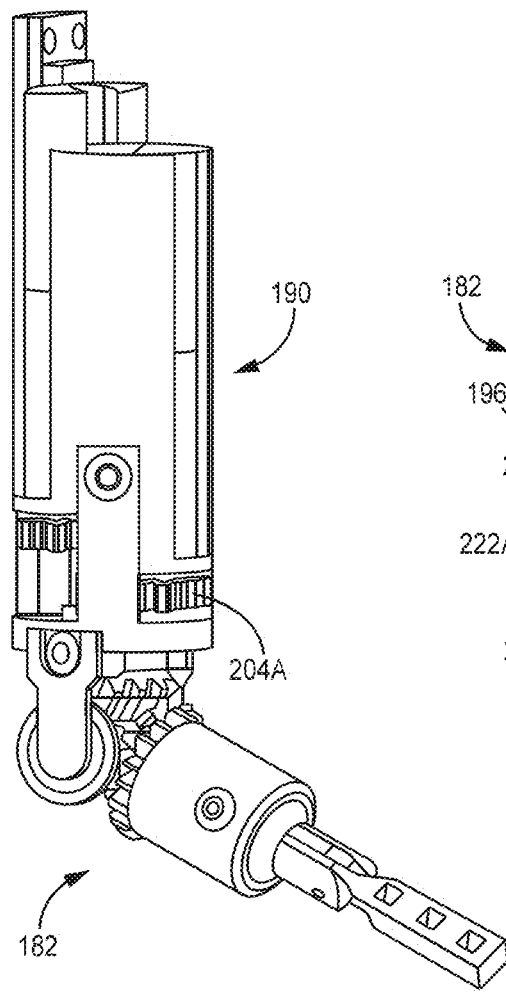
FIG. 7A is a side view of the forearm of FIG. 6A, according to one embodiment.
Figure 7B:
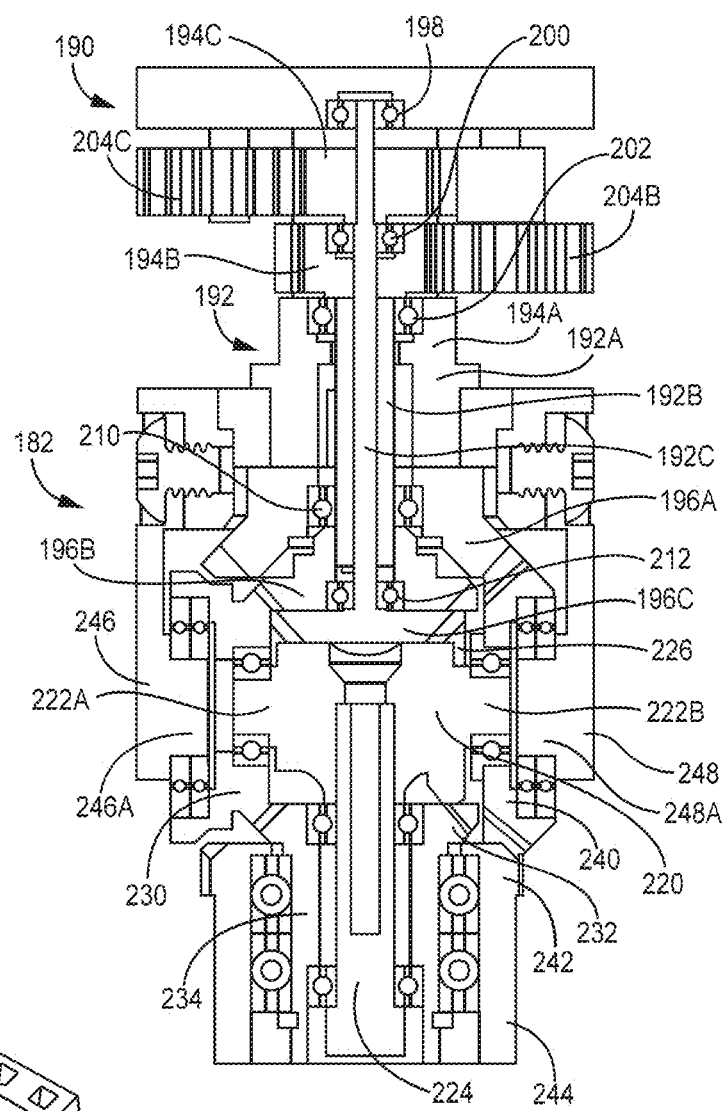
FIG. 7B is a cross-sectional cutaway side view of a portion of the forearm and the wrist joint of the forearm of FIG. 6A, according to one embodiment.

One embodiment of the wrist joint 182 is depicted in additional detail in FIGS. 7A and 7B. More specifically, FIG. 7B depicts a cross-sectional front view of the distal portion of the forearm body 190 and the wrist joint 182 in which certain internal components are visible, according to one exemplary embodiment. The forearm body 190 has a set of nested driveshafts 192 rotatably disposed within the body 190 that extend into the wrist joint 182. The set of nested driveshafts 192 is made up of a first or outer driveshaft 192A, a second or middle driveshaft 192B, and a third or inner driveshaft 192C. The set of nested driveshafts 192 extend from the forearm body 190 into the wrist joint 182 as shown. The inner driveshaft 192C is rotatably disposed within the middle driveshaft 192B as shown, and has a driven gear 194C fixedly or integrally attached at its proximal end. At its distal end, the inner driveshaft 192C is rotatably coupled to a first or inner drive bevel gear 196C. The middle driveshaft 192B is rotatably disposed within the outer driveshaft 192A as shown, and has a driven gear 194B fixedly or integrally attached at its proximal end. At its distal end, the middle driveshaft 192B is coupled to a second or middle drive bevel gear 196B. The outer driveshaft 192A is rotatably disposed within the forearm body 190 and wrist 182 and has a driven gear 194A fixedly or integrally attached at its proximal end. At its distal end, the outer driveshaft 192A is coupled to a first or outer drive bevel gear 196A.

Continuing with FIG. 7B, the proximal end of the inner driveshaft 192C is rotatably supported in the forearm body 190 via a first shaft bearing 198 and a second shaft bearing 200. Further, the proximal end of the middle driveshaft 192B, including the driven gear 194B, is rotatably supported via the second shaft bearing 200 and a third shaft bearing 202. In addition, the proximal end of the outer driveshaft 192A, including driven gear 194A, is rotatably supported via the third shaft bearing 202.

The set of nested driveshafts 192 has three motors operably coupled thereto. More specifically, motor 186B (of FIG. 6C) has an motor drive gear 204A (shown in FIG. 7A, but not visible in FIG. 7B) that is coupled to the driven gear 194A (which is coupled to the outer driveshaft 192A). Further, motor 186A (of FIG. 6C) has a motor drive gear 204C that is coupled to the driven gear 194C (which is coupled to the inner driveshaft 192C). In addition, motor 186C (of FIG. 6C) has a motor drive gear 204B (also not visible in the figures) that is coupled to the driven gear 194B (which is coupled to the middle driveshaft 192B).

Thus, in operation, the motor 186B can be actuated to drive rotation of the outer driveshaft 192A by driving rotation of motor drive gear 204A, which drives rotation of the driven gear 194A. Similarly, the motor 186C can be actuated to drive rotation of the middle driveshaft 192B by driving rotation of motor drive gear 204B (also not visible), which drives rotation of the driven gear 194B. In a similar fashion, the motor 186A can be actuated to drive rotation of the inner driveshaft 192C by driving rotation of motor drive gear 204C, which drives rotation of the driven gear 194C.

At the distal end, the outer driveshaft 192A and outer drive bevel gear 196A are supported by the first wrist bearing 210. In addition, the middle driveshaft 192B and the middle drive bevel gear 196B are supported by the first wrist bearing 210 and the second wrist bearing 212.

The inner drive bevel gear 196C is rotatably coupled to a differential yoke 220 having two rotational projections 222A, 222B, an extension shaft 224 that extends into the end effector body 244, and a yoke bevel gear 226. The differential yoke 220 is similar to the differential yoke 56C of the shoulder joint 46 discussed above and thus conveys the same or similar in-line benefits to those of the yoke 56C, including the minimal cross-sectional profile and the in-line configuration as discussed in detail above. The inner drive bevel gear 196C rotatably couples to the yoke bevel gear 226. As such, rotation of the inner drive bevel gear 196C causes the rotation of the differential yoke 220 around the rotational projections 222A, 222B such that the extension shaft 224 is caused to rotate around the longitudinal axis of the yoke 220 that extends from the first rotational projection 222A to the second 222B.

The middle drive bevel gear 196B is rotatably coupled to a first wrist bevel gear 230, which is rotatably disposed over the first inner rotational projection 222A. In addition, the first wrist bevel gear 230 is also rotatably disposed over the first outer rotational projection 246A extending from the first wrist support bracket 246. The first wrist support bracket 246 extends from the distal end of the forearm body 190. As such, the first wrist bevel gear 230 is rotatably supported by the first inner rotational projection 222A and the first outer rotational projection 246A. Further, the first wrist bevel gear 230 is rotatably coupled to the end effector output bevel gear 232, which is coupled to or integral with the end effector output body 234. Thus, rotation of the middle drive bevel gear 196B causes rotation of the first wrist bevel gear 230, which causes rotation of the end effector output bevel gear 232, which causes rotation of the end effector output body 234. In certain embodiments, the output body 234 is operably coupled to the end effector to actuate the end effector in some fashion, depending on the type of end effector.

The outer drive bevel gear 196A is rotatably coupled to the second wrist bevel gear 240, which is rotatably disposed over the second inner rotational projection 222B. In addition, the second wrist bevel gear 240 is also rotatably disposed over the second outer rotational projection 248A extending from the second wrist support bracket 248. The second wrist support bracket 248 extends from the distal end of the forearm body 190 in a fashion similar to the first wrist support bracket 246. As such, the second wrist bevel gear 240 is rotatably supported by the second inner rotational projection 222B and the second outer rotational projection 248A. Further, the second wrist bevel gear 240 is rotatably coupled to the end effector rotation bevel gear 242, which is coupled to or integral with the end effector body 244. Thus, rotation of the outer drive bevel gear 196A causes rotation of the second wrist bevel gear 240, which causes rotation of the end effector rotation bevel gear 242, which causes rotation of the end effector body 244, thereby causing rotation of the end effector around its longitudinal axis.

The wrist joint embodiment 182 discussed above is a compact dexterous wrist joint. Given the unpredictable nature of a patient's anatomy, the criticality of a robotic device providing as much control as possible to a surgeon for the purpose of completing a surgical task, and the importance of tool dexterity in surgical procedures, the dexterity of the wrist joint in a robotic arm is important. There are known devices that provide a wrist joint with seven degrees of freedom, but those devices have arm and end effector actuation via actuators (which are typically motors) disposed outside the patient's body, such as, for example, the EndoWrist® of the Da Vinci® system. The use of mechanical (cables, etc.), pneumatic, hydraulic, or other such force transmission systems make it possible for the EndoWrist and other such devices to maintain a smaller profile while having great dexterity. In contrast, to date, known devices having actuators (such as motors) disposed within the patient's body or the opening through which the device is positioned have not been able to approach that number of degrees of freedom or the corresponding amount of dexterity. However, the wrist embodiments (such as wrist joint 182) provide additional dexterity in comparison to other known devices with internal actuators. That is, the wrist joint 182 provides three degrees of freedom while minimizing its cross-sectional profile due to the joint 182 configuration. More specifically, as mentioned above, the configuration of the wrist joint 182 with the differential yoke 220 that is similar to the differential yoke 56C of the shoulder joint 46 results in similar features and functionality, including the minimal cross-sectional diameter and the in-line configuration.

Figure 8A:
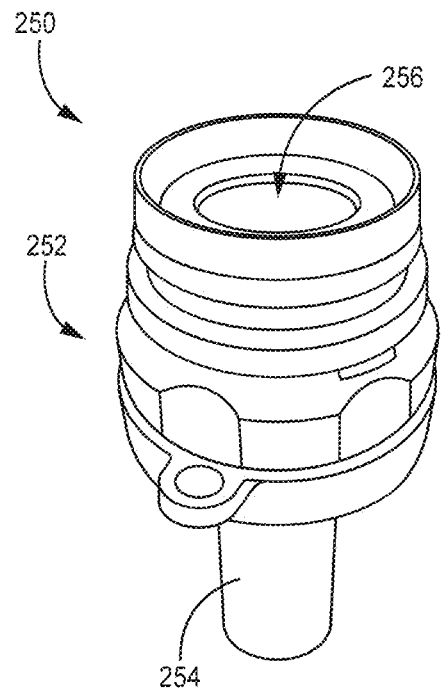
FIG. 8A is a perspective view of a laparoscopic trocar, according to one embodiment.
Figure 8B:
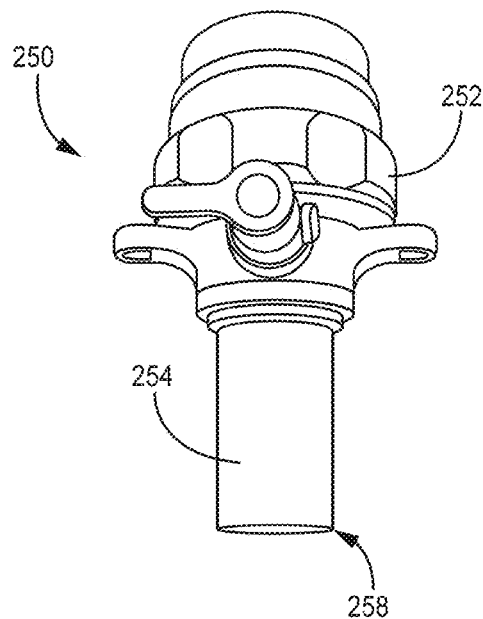
FIG. 8B is a side view of the laparoscopic trocar of FIG. 8A, according to one embodiment.

FIGS. 8A and 8B depict one example of a trocar 250 according to one embodiment that is sized and configured to allow for receiving therethrough the various robotic device embodiments disclosed or contemplated herein. The trocar 250 has a port (or "seal") 252 and a cannula 254 extending from the port 252. The port 252 and cannula 254 define an inner lumen 256 having a diameter that is large enough to receive any arm and internal body of any device implementation disclosed or contemplated herein. Further, the cannula 254 has a length such that the shoulder joint of the robotic device positioned therethrough extends through and is positioned distally out of the distal end 258 of the cannula 254, thereby allowing the arm coupled to the shoulder joint to move in any direction as desired without being hindered or obstructed by the cannula 254. As also discussed elsewhere herein, in addition to this trocar 250 and any other known laparoscopic trocar, it is understood that any insertion device of the appropriate size (including any type of port) or any incision of the appropriate size can be used with the various device embodiments disclosed or contemplated herein.

Trocar ports such as the trocar 250 described above and other known trocars can have certain advantages over known single-site entry ports. For example, insertion of certain known robotic devices through the single-site entry port can cause structural damage to the robotic device as a result of the physical contact between the port and the device. In addition, such known single-site entry ports require a larger incision in the patient than standard trocars require.

Figure 9A:
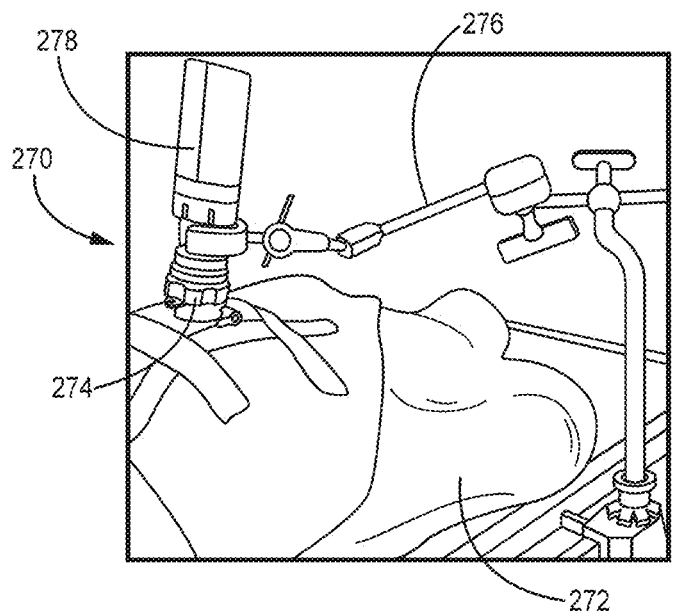
FIG. 9A is a perspective exterior view of a one-armed robotic device positioned within a target cavity of a patient, according to one embodiment.
Figure 9B:
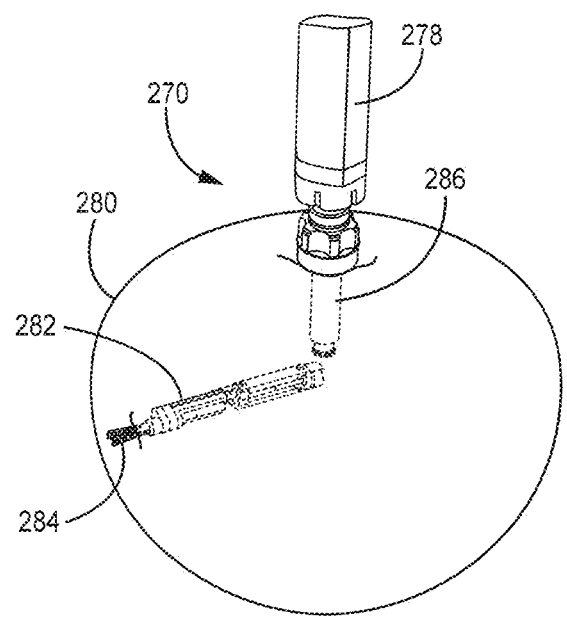
FIG. 9B is a schematic view of the calculated workspace of the one-armed robotic device of FIG. 9A, according to one embodiment.

In use, one embodiment of a single-arm robotic device 270 is depicted in FIGS. 9A and 9B in a surgical environment. More specifically, FIG. 9A provides an external view of the device 270 positioned in a patient 272 through a trocar 274 such that the device 270 is in its operational configuration. That is, the device 270 is positioned into the target cavity (not shown) of the patient 272 such that the robotic arm (not shown) can be used to perform the desired procedure therein. In this embodiment, the device 270 is stabilized and/or maintained in the desired operational position via a known external support 276 that is coupled to the external body 278 of the device 270.

Further, FIG. 9B is a schematic view of the device 270 and the visual representation of the workspace 280 in which the device 270 can operate. More specifically, the workspace 280 is the visual representation of the full area that the end effector 284 coupled to the single arm 282 can reach. As such, the device 270 can be positioned within a target cavity in a patient such as the patient 272 in FIG. 9B such that the interior body 286 extends into the target cavity, resulting in the robotic arm 282 being disposed therein. In this specific embodiment, the device 270, which has components and functionality similar to the various other device embodiments disclosed or contemplated herein, can manipulate or otherwise position the arm 282 such that the end effector 284 can extend to all of the areas defined by the workspace 280. Thus, the end effector 284 can be used to perform a procedure at any location within that workspace 280.

Although the present invention has been described with reference to preferred embodiments, persons skilled in the art will recognize that changes may be made in form and detail without departing from the spirit and scope of the invention.

What is claimed is:

1. A robotic device comprising:
    (a) an elongate device body comprising:
        (i) a proximal section comprising a proximal section diameter; and
        (ii) a distal section comprising a distal section diameter, wherein the distal section diameter is less than the proximal section diameter;
    (b) a first driveshaft operably coupled to a first motor;
    (c) a second driveshaft operably coupled to a second motor;
    (d) a first bevel gear operably coupled to the second driveshaft at a distal end of the second driveshaft;
    (e) a shoulder joint comprising:
        (i) a differential yoke rotationally coupled to the first driveshaft, the differential yoke comprising a yoke body and a pair of curved shells extending therefrom and defining a yoke lumen, wherein the yoke lumen has a longitudinal axis that is transverse to the longitudinal axis of the yoke body, and wherein the differential yoke rotates around a first rotational axis; and
        (ii) a dual shaft rotatably disposed within the yoke lumen, the dual shaft comprising:
            (A) a rotational shaft rotatably disposed within the yoke lumen, the rotational shaft rotationally coupled to the first bevel gear, wherein the rotational shaft rotates around a second rotational axis; and
            (B) an extension shaft extending from the rotational shaft such that a longitudinal axis of the extension shaft is transverse to a longitudinal axis of the rotational shaft; and
        (iii) an output body rotatably disposed around the extension shaft such that the extension shaft is rotatably disposed within a lumen of the output body, and wherein the output body rotates around a third rotational axis,
    wherein the first, second, and third rotational axes intersect at a single point.

2. The robotic device of claim 1, wherein the first and second motors are disposed within the elongate body.

3. The robotic device of claim 1, wherein the extension shaft is fixedly attached to the rotational shaft.

4. The robotic device of claim 1, further comprising a third driveshaft operably coupled to a third motor, the third driveshaft operably coupled at a distal end to a second bevel gear, wherein the second bevel gear is operably coupled to the output body.

5. The robotic device of claim 1, further comprising an arm operably coupled to the output body.

6. The robotic device of claim 1, wherein the shoulder joint is a unitary shoulder joint.

7. The robotic device of claim 1, wherein the distal section is sized and structured to be positionable through a trocar port.

8. A robotic device comprising:
    (a) an elongate device body comprising:
        (i) a proximal section comprising a proximal section diameter;
        (ii) a distal section comprising a distal section diameter, wherein the distal section diameter is less than the proximal section diameter; and
    (b) a first driveshaft operably coupled to a first motor;
    (c) a second driveshaft operably coupled to a second motor, the second driveshaft coaxial with the first driveshaft and operably coupled at a distal end to a first bevel gear;
    (d) a shoulder joint comprising:
        (i) a differential yoke rotationally coupled to the first driveshaft, the differential yoke comprising a yoke body and a yoke lumen defined in the differential yoke, wherein the lumen has a longitudinal axis that is transverse to the longitudinal axis of the yoke body; and
        (ii) a dual shaft rotatably disposed within the yoke lumen, the dual shaft comprising:
            (A) a rotational shaft rotatably disposed within the yoke lumen, the rotational shaft rotationally coupled to the first bevel gear; and
            (B) an extension shaft extending from the rotational shaft such that a longitudinal axis of the extension shaft is transverse to a longitudinal axis of the rotational shaft; and
        (iii) an output body rotatably disposed around the extension shaft such that the extension shaft is rotatably disposed within a lumen of the output body,
    wherein the shoulder joint is an in-line joint that is collinear with the distal section.

9. The robotic device of claim 8, wherein the first and second motors are disposed within the elongate body.

10. The robotic device of claim 8, further comprising an arm operably coupled to the output body.

11. The robotic device of claim 8, wherein the yoke lumen is defined by opposing first and second yoke lumen walls, the first yoke lumen wall comprising a first slot and the second yoke lumen wall comprising a second slot.

12. The robotic device of claim 11, wherein the extension shaft is positionable within the first and second slots.

13. A robotic device comprising:
(a) a first driveshaft disposed through an elongate device body and operably coupled to a first motor;
(b) a second driveshaft disposed through the elongate device body and operably coupled to a second motor, the second driveshaft operably coupled at a distal end to a first shoulder gear;
(c) a third driveshaft disposed through the elongate device body and operably coupled to a third motor, the third driveshaft operably coupled at a distal end to a second shoulder gear; and
(d) a shoulder joint comprising:
(i) a differential yoke rotationally coupled to the first driveshaft, the differential yoke comprising a yoke lumen defined in the differential yoke; and
(ii) a T shaft rotatably disposed within the yoke lumen, the T shaft comprising:
(A) a rotational shaft rotatably disposed within the yoke lumen, the rotational shaft rotationally coupled to the first shoulder gear; and
(B) an extension shaft extending from the rotational shaft;
(iii) an output body rotatably disposed over the extension shaft and having an output body gear, the output body gear rotationally coupled to the second shoulder gear, wherein the first shoulder gear defines a radial outer limit of the shoulder joint.

14. The robotic device of claim 13, wherein the first, second, and third motors are disposed within the elongate device body.

15. The robotic device of claim 13, wherein the yoke lumen is defined by opposing first and second yoke lumen walls, the first yoke lumen wall comprising a first slot and the second yoke lumen wall comprising a second slot.

16. The robotic device of claim 15, wherein the extension shaft is positionable within the first and second slots.

17. The robotic device of claim 13, wherein a longitudinal axis of the extension shaft is transverse to a longitudinal axis of the rotational shaft.

18. The robotic device of claim 13, further comprising an arm operably coupled to the output body.

19. The robotic device of claim 18, wherein the arm comprises an upper arm body; a forearm body; an elbow joint coupling the forearm body to the upper arm body; an end effector; and a wrist joint coupling the end effector to the forearm body, wherein the upper arm body is operably coupled to the output body.

20. The robotic device of claim 13, wherein the first driveshaft is disposed within the third driveshaft, and wherein the third driveshaft is disposed within the second driveshaft.

* * * * *